(12) United States Patent
Salehi

(10) Patent No.: US 10,098,991 B2
(45) Date of Patent: Oct. 16, 2018

(54) SELF-CLEANING SURGICAL SUCTION DEVICE AND METHOD OF USE

(71) Applicant: NEUROENTERPRISES, LLC, Port Barrington, IL (US)

(72) Inventor: Sean A. Salehi, Chicago, IL (US)

(73) Assignee: NEUROENTERPRISES, LLC, Chicago, IL (US)

( * ) Notice: Subject to any disclaimer, the term of this patent is extended or adjusted under 35 U.S.C. 154(b) by 512 days.

(21) Appl. No.: 14/737,105

(22) Filed: Jun. 11, 2015

(65) Prior Publication Data

US 2015/0359950 A1    Dec. 17, 2015

Related U.S. Application Data

(63) Continuation-in-part of application No. 13/738,650, filed on Jan. 10, 2013, now Pat. No. 9,144,636, which is a continuation-in-part of application No. 13/420,542, filed on Mar. 14, 2012, now Pat. No. 8,986,285.

(60) Provisional application No. 62/150,070, filed on Apr. 20, 2015, provisional application No. 61/464,922, filed on Mar. 14, 2011.

(51) Int. Cl.
    *A61M 1/00* (2006.01)
    *A61C 17/06* (2006.01)
    *A61B 90/70* (2016.01)

(52) U.S. Cl.
    CPC ......... *A61M 1/0086* (2014.02); *A61C 17/043* (2013.01); *A61M 1/008* (2013.01); *A61M 1/0047* (2013.01); *A61B 90/70* (2016.02); *A61M 2209/10* (2013.01)

(58) Field of Classification Search
    CPC .. A61M 1/0086; A61M 1/0047; A61M 1/008; A61M 1/0039; A61C 17/043
    See application file for complete search history.

(56) References Cited

U.S. PATENT DOCUMENTS

| 3,375,828 A | 4/1968 | Sheridan ................ 128/351 |
| 3,958,573 A * | 5/1976 | Wiley .................. A61C 17/04 604/267 |

(Continued)

OTHER PUBLICATIONS

European Search Report issued in corresponding foreign application, EP 12758041.3 pp. 1-8 (dated Nov. 11, 2015).

(Continued)

*Primary Examiner* — Ariana Zimbouski
(74) *Attorney, Agent, or Firm* — J. Peter Paredes; David G. Rosenbaum; Rosenbau, IP, P.C.

(57) ABSTRACT

A surgical suction device is disclosed that includes a suction tube having a first longitudinal axis, a proximal opening, and a distal opening; a guide tube that is substantially coextensive with and parallel to the suction tube, and has a second longitudinal axis, a proximal opening, and a distal opening; a stylet having a proximal end and a distal end; and a junction point having a proximal opening and a distal opening; wherein the stylet is disposed along the second longitudinal axis and encircled by the guide tube, and urging the stylet through the guide tube along the second longitudinal axis through the junction conduit translates the distal end of the stylet to the distal opening of the junction point. The guide tube may effectively cut the length of the handle member in half.

3 Claims, 19 Drawing Sheets

(56) References Cited

U.S. PATENT DOCUMENTS

| | | | |
|---|---|---|---|
| 4,022,218 A | 5/1977 | Riddick | 128/350 |
| 4,204,328 A | 5/1980 | Kutner | 433/29 |
| 4,699,138 A | 10/1987 | Behrstock | 128/207.16 |
| 4,886,492 A | 12/1989 | Brooke | 604/49 |
| 5,195,952 A | 3/1993 | Solnit et al. | 604/19 |
| 5,320,110 A | 6/1994 | Wang | 128/753 |
| 5,591,141 A | 1/1997 | Nettekoven | 604/280 |
| 5,643,229 A | 7/1997 | Sinaiko | 604/267 |
| 5,779,649 A | 7/1998 | Herbert | 600/571 |
| 6,045,516 A | 4/2000 | Phelan | 600/579 |
| 6,146,136 A | 11/2000 | Tenniswood | 433/92 |
| 6,881,060 B2 | 4/2005 | Lundgren | 433/91 |
| 6,908,455 B2 | 6/2005 | Hajianpour | 604/266 |
| D571,458 S | 6/2008 | Kataoka et al. | D24/108 |
| 8,574,222 B2 * | 11/2013 | Hensler | A61M 1/0041 604/101.01 |
| 2004/0111082 A1 | 6/2004 | Howell et al. | 606/2.5 |
| 2006/0264988 A1 | 11/2006 | Boyle | 606/159 |
| 2007/0219499 A1 | 9/2007 | Hayakawa et al. | 604/164.01 |

OTHER PUBLICATIONS

International Search Report issued in corresponding foreign application, PCT application PCT/US2012/029131, pp. 1-3 (dated Oct. 12, 2012).

Preliminary Report on Patentability issued in corresponding foreign application, PCT application PCT/US2012/029131, pp. 1-5 (dated Sep. 26, 2013).

Written Opinion issued in corresponding foreign application, PCT application PCT/US2012/029131, pp. 1-3 (dated Oct. 12, 2012).

USPTO, "Continuity Tab" printout for U.S. Appl. No. 13/738,650 as accessed on Mar. 17, 2016, 1 page.†

USPTO, "Updated Filing Receipt" issued in file history of U.S. Appl. No. 13/738,650 on Apr. 18, 2013, published Sep. 19, 2013, 3 pages.†

\* cited by examiner
† cited by third party

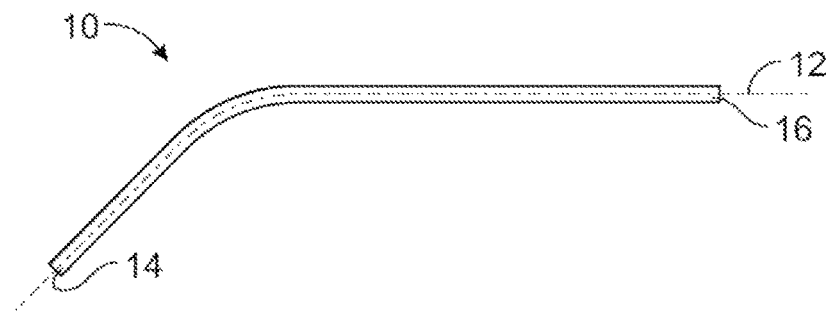
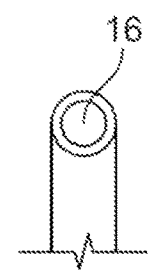
FIG. 2a  FIG. 2b
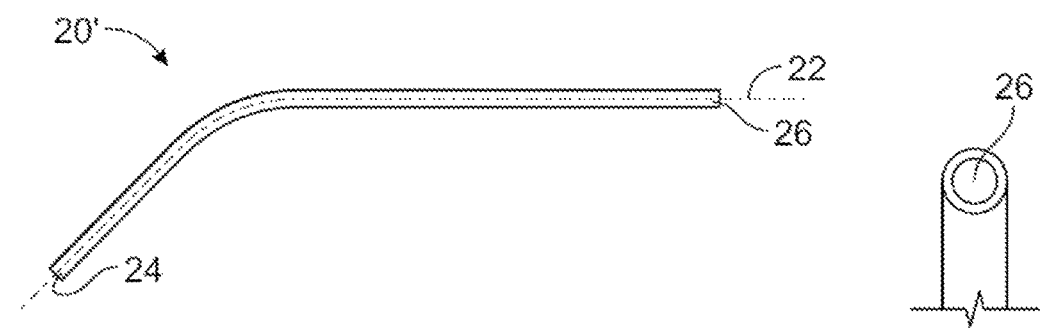
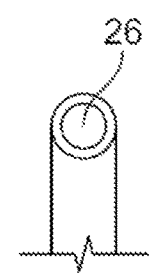
FIG. 3a  FIG. 3b
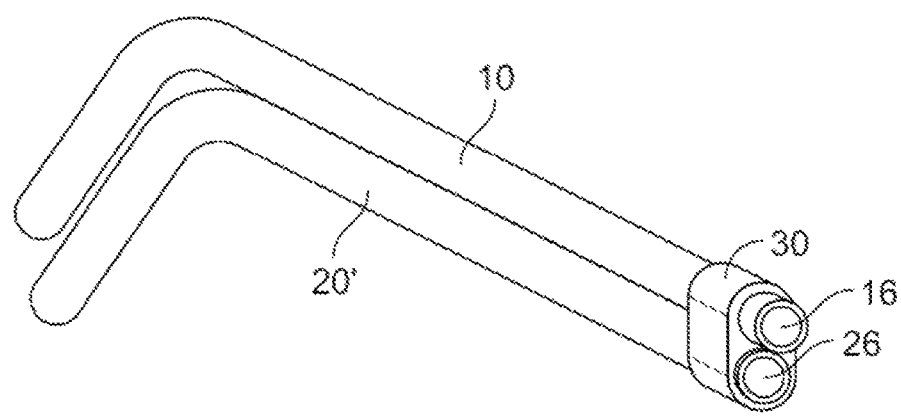
FIG. 4

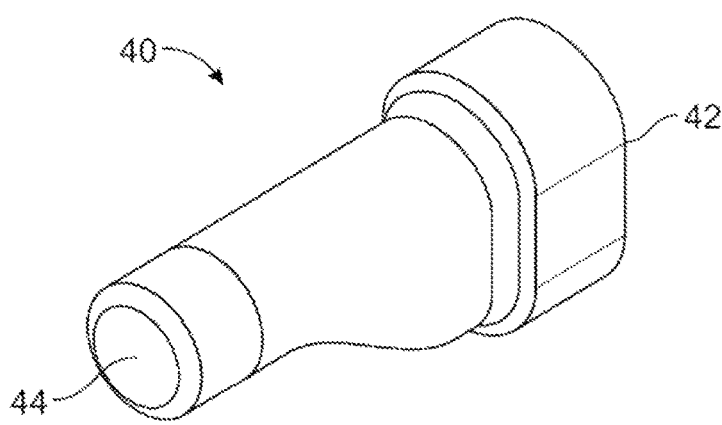
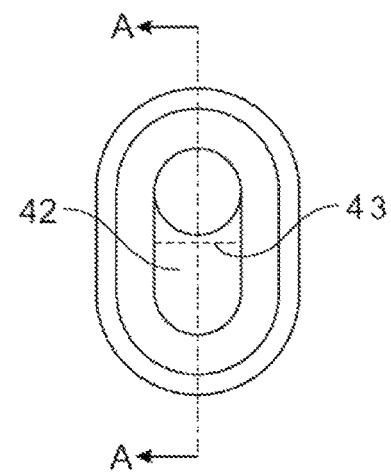
FIG. 5a
FIG. 5b
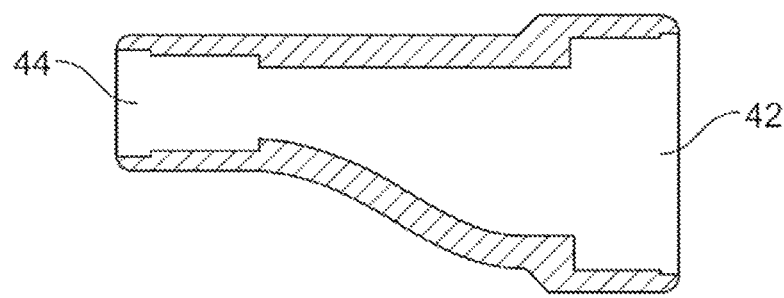
FIG. 5c
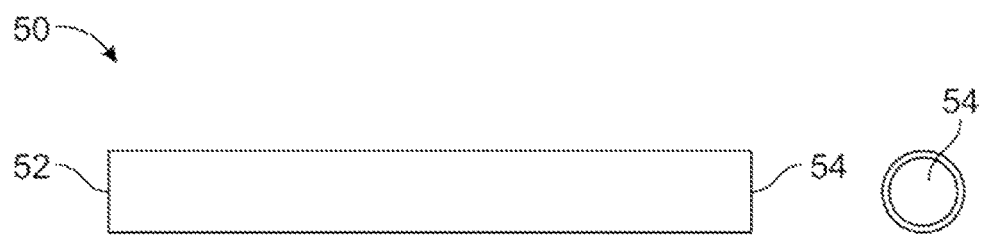
FIG. 6

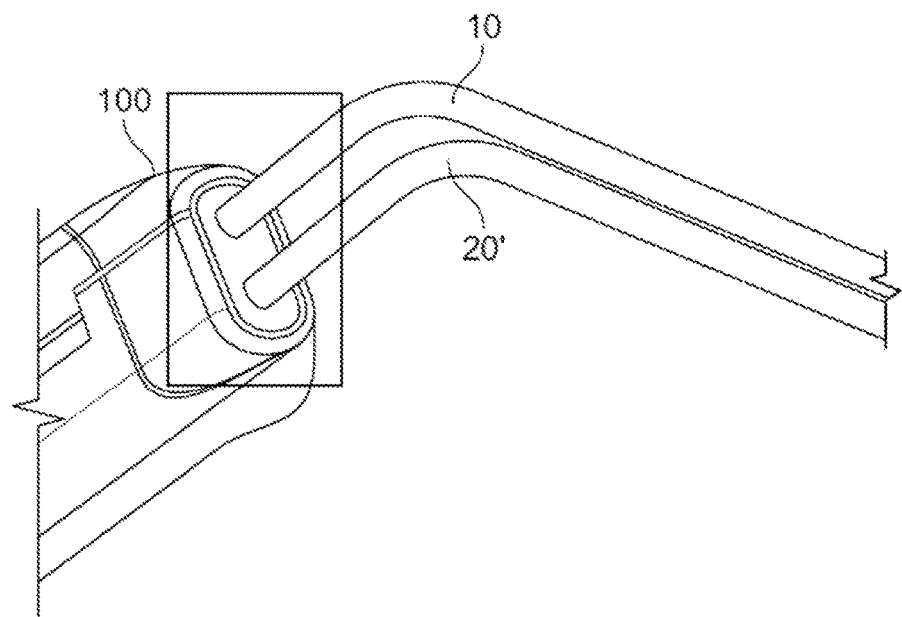
FIG. 12
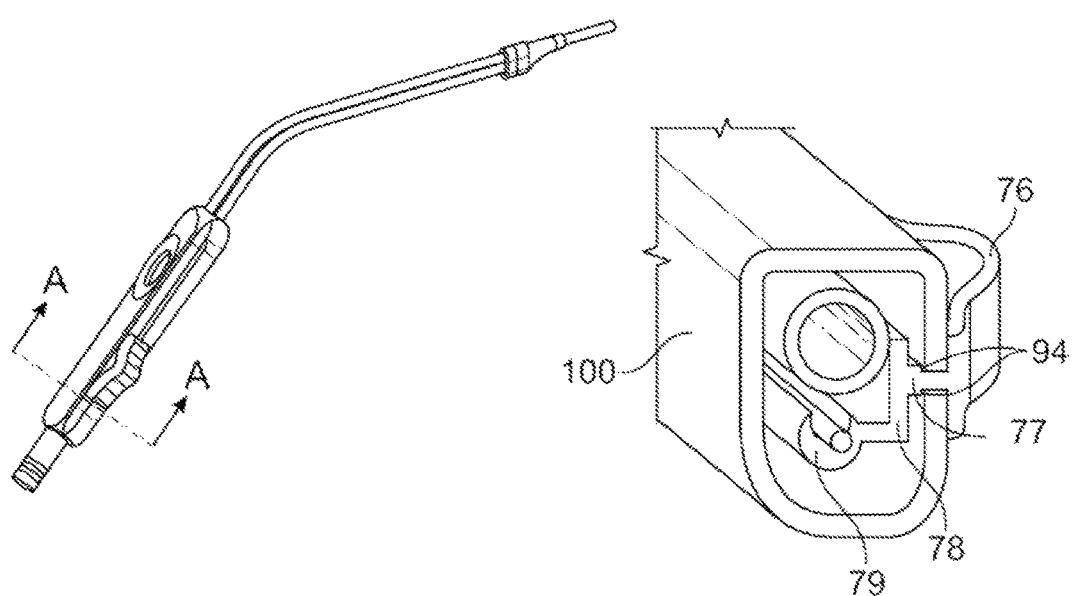
FIG. 13                     SECTION A-A

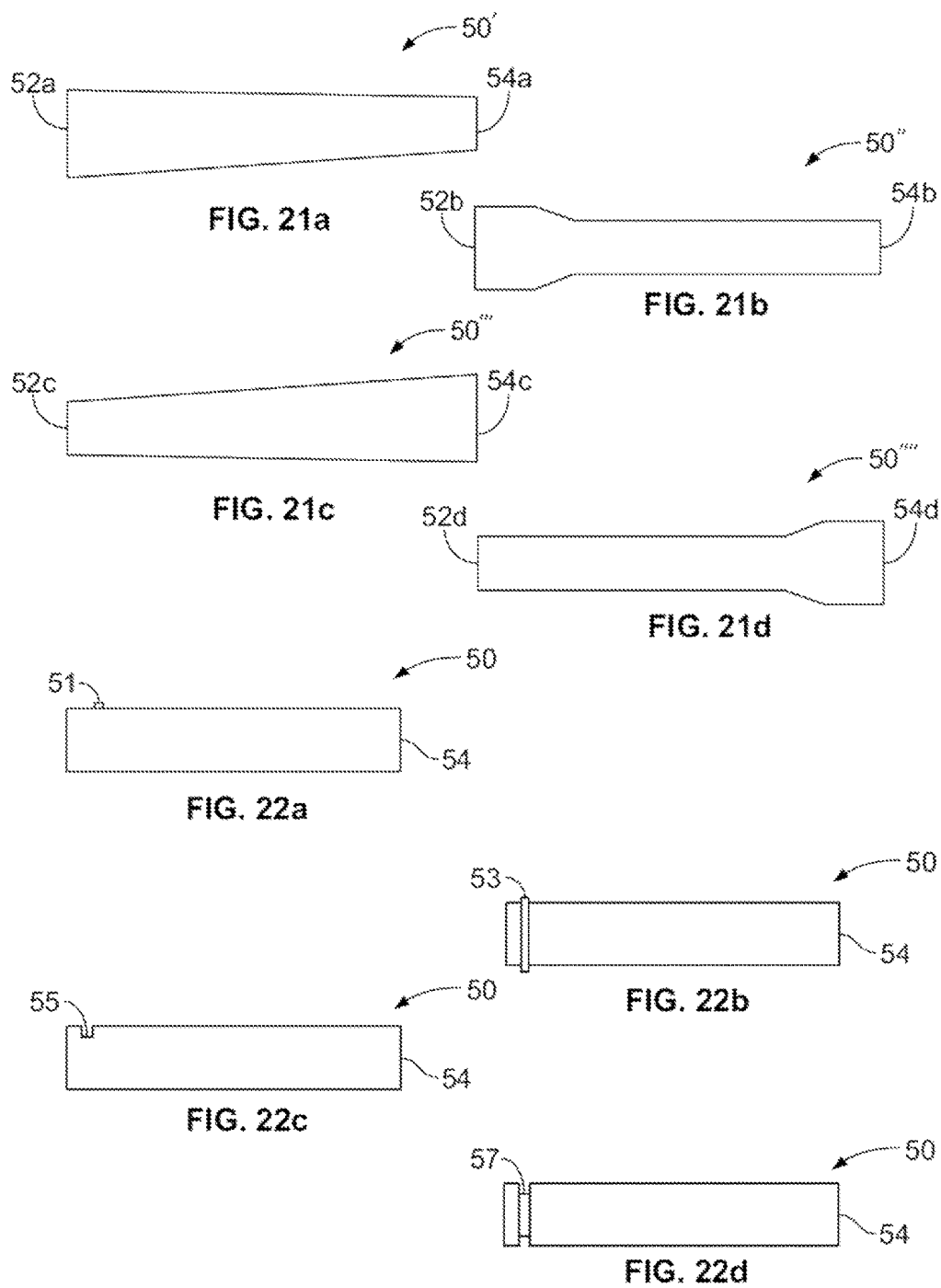

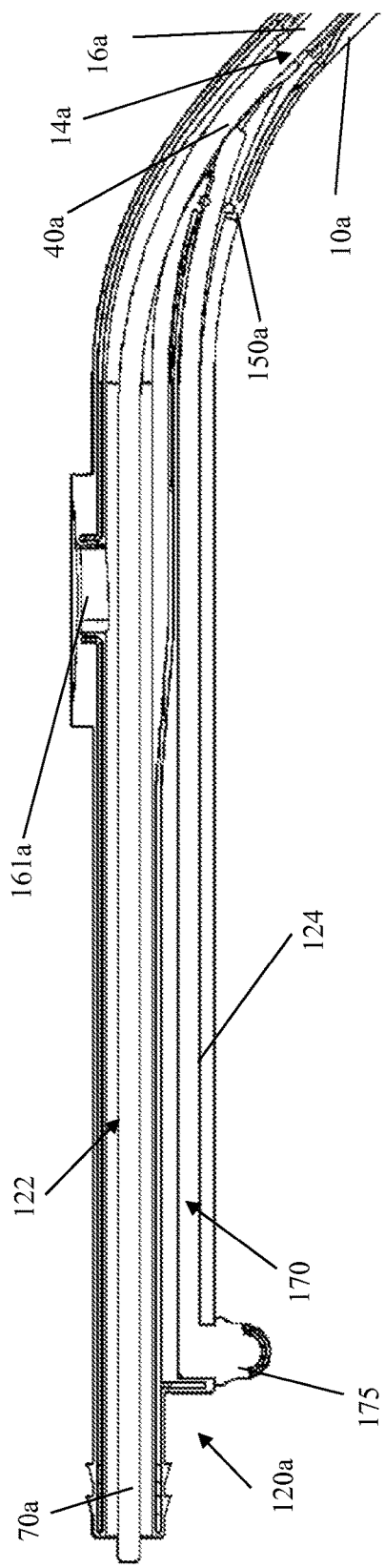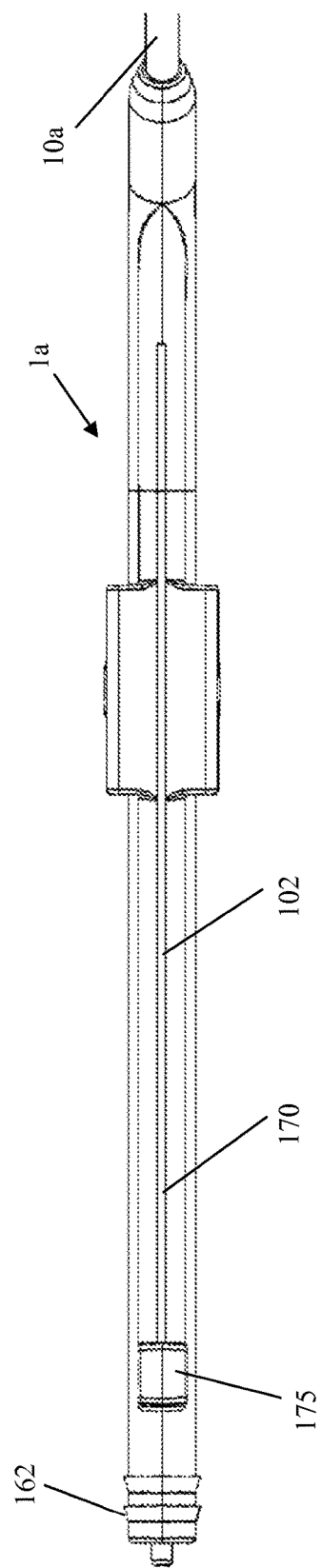
FIG. 24C
FIG. 24D

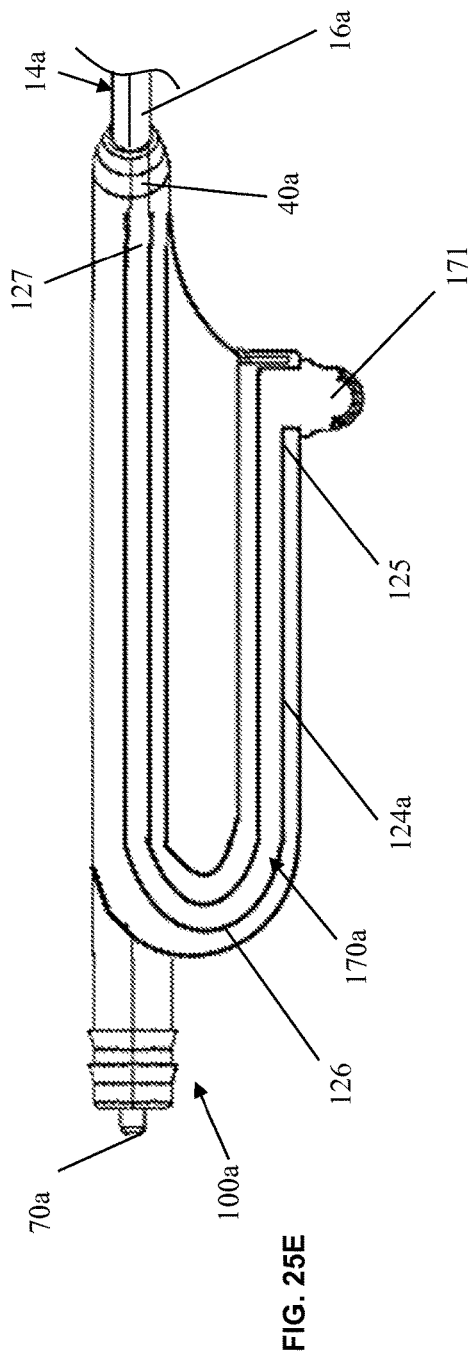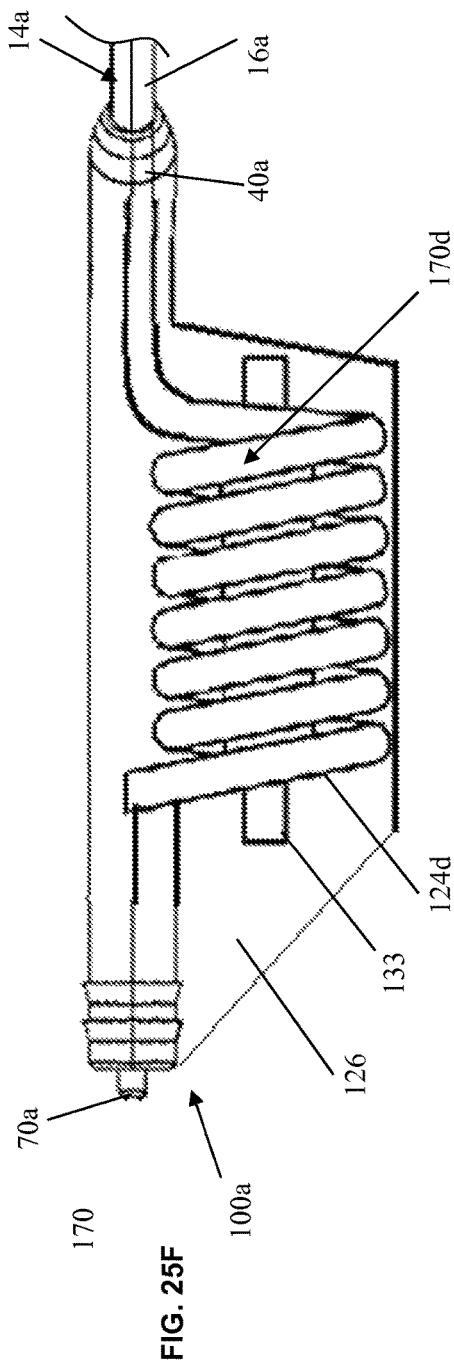

SELF-CLEANING SURGICAL SUCTION DEVICE AND METHOD OF USE

CROSS-REFERENCES TO RELATED APPLICATIONS

This application claims priority to U.S. Provisional Application Ser. No. 62/150,070, filed Apr. 20, 2015, and is a continuation-in-part claiming benefit of U.S. patent application Ser. No. 13/738,650, filed Jan. 10, 2013, which is a continuation-in-part of U.S. patent application Ser. No. 13/420,542, filed Mar. 14, 2012, now U.S. Pat. No. 8,986,285, which claims priority to U.S. Provisional Application Ser. No. 61/464,922, filed Mar. 14, 2011, all of which are hereby incorporated by reference in their respective entireties.

FIELD OF THE INVENTION

The present invention relates to the field of surgical instruments employed for removing debris from within a surgical operative field. In particular, the present invention is a tubular suction device for surgical, dental, or veterinary use that includes a means for self-clearing debris from its intake portion.

BACKGROUND

A common requirement for any surgical procedure on a patient is that the operative field opened in the patient must be continually cleared of fluids and particulates that obscure the surgeon's vision of the field. These fluids and particulates can include blood, irrigating solution, bone chips or dust, hemostatic agents, among others. Irrespective of the region of the body where the surgery occurs, but especially with respect to neurological or orthopedic procedures, significant amounts of these fluids and particulates present challenges to the surgeon's clear viewing of the surgical field. In addition to the fluids and particulates derived from the patient, foreign materials usefully employed as hemostatic agents can also obscure the operative field and require removal. Such hemostatic agents include absorbable gelatin sponges (e.g., Gelfoam from Baxter Healthcare Corporation), a kneadable mixture of beeswax and mineral wax (e.g., Ethicon Bone Wax from Johnson & Johnson), or an oxidized cellulose polymer (e.g., a polymer of polyanhydroglucuronic acid sold under the trade name Surgicel by Johnson & Johnson).

Removing these materials is typically accomplished using a surgical suction device, inserting the distal tip of the surgical suction device in and about the operative field whereupon the field-obscuring materials are sucked away to a location outside of the field; until, that is, the distal tip becomes fouled by particulate matter or coagulated blood or combinations of such, which is inevitable.

The distal tip is commonly referred to as a surgical suction tip and is an integral part of any surgical procedure. More particularly to the general view of the problem presented above, the suction tip is connected to a wall suction unit in the surgical suite via a plastic tubing. The suction (referred to below as negative pressure) created at the tip clears the field of the materials mentioned above that may be obstructing the surgeon's field of view.

The practical approach taken in a surgery to clear the clogged suction tips is to interrupt the surgery so the tip can be cleaned. Literally, the surgeon stops clearing the operative field, hands the clogged suction to the scrub nurse so s/he can clear it with saline flushes or a stylet (i.e., an implement employed to poke at and remove obstructing matter from a vacuum path). This process may have to be repeated multiple times in a surgery, prolonging the surgical time and contributing a significant source of inefficiency to the surgical procedure.

Despite the development of various shapes of the suction tip inspired by the desire to eliminate the clogged distal tip problem, clogging of the suction tip remains a problem in all operating rooms. Accordingly, the surgeon uses the surgical suction device until its distal tip becomes clogged, hands it to an assistant who, under sterile conditions, manually replaces or unclogs the tip and hands the surgical suction device back to the surgeon. Obviously, critical time is lost by the need to hand the surgical suction device to an assistant for clearance, and then get it back, and then place it where it can do its intended task until, alas, the cycle is repeated with the distal tip yet again clogged, lost time, and a patient in surgery longer than necessary.

It would be desirable to have a surgical suction device designed that allowed the surgeon to clear the distal tip directly without need to pass it off to another or otherwise lose time completing the work of addressing the patient's issues that caused the opening of the operative field in the first place.

SUMMARY

A suction device is generally disclosed and comprises: a suction tube having a first longitudinal axis, a proximal opening, a distal opening, and a suction lumen disposed therebetween; a guide structure having a first guide lumen and a second guide lumen, wherein the first guide lumen is coaxial with the suction lumen; a stylet having a proximal end and a distal end, wherein the stylet is coaxially disposed within the second guide lumen, wherein the second guide lumen includes a proximal end, a middle section, and a distal end, and the middle section includes a substantially U-shape portion and the stylet is longitudinally translatable through the middle section; a junction point intersecting the distal opening of the first guide lumen and the distal opening of the second guide lumen, and axial movement of the stylet through the second guide lumen along the second longitudinal axis through the junction point translates the distal end of the stylet into the suction lumen.

The foregoing and other features and advantages of the invention are apparent from the following detailed description of embodiments read in conjunction with the accompanying drawings. The detailed description and drawings are merely illustrative of the invention rather than limiting. The scope of the invention is defined by the appended claims and equivalents thereof. It is intended that all changes or modification within the meaning and range of equivalents are embraced by the claims.

BRIEF DESCRIPTION OF THE DRAWINGS

FIG. 1b is a perspective blown up view of the embodiment of the self-cleaning surgical suction device depicted in FIG. 1a.

FIG. 2a is a profile view of a guide structure employed in one embodiment of the present invention.

FIG. 2b is a frontal view from the distal end of the suction tube depicted in FIG. 2a.

FIG. 3a is a profile view of a guide tube employed in one embodiment of the present invention.

FIG. 3b is a frontal view from the distal end of the guide tube depicted in FIG. 3a.

FIG. 4 is a perspective view of one embodiment wherein the distal end of the suction tube extends beyond the distal opening of the bracket.

FIG. 5a is a perspective view of the junction element.

FIG. 5b is a frontal view of the proximal opening of the junction conduit.

FIG. 5c is a cross sectional view of the junction conduit along section A-A.

FIG. 6 is a profile view and frontal view of the tubular tip.

FIG. 12 is a perspective view illustrating the nearness of the distal dorsal recess and distal ventral recess to the outer wall of the distal attachment region once attachment of the handle piece is completed.

FIG. 13 is a perspective cross sectional view along section A-A of a tubular member, stylet, and knob assembled and disposed within a completed handle piece.

FIGS. 21a-d each show a series of profile views of alternative embodiments of the tubular tip in accordance with the present invention.

FIGS. 22a-d each show a series of profile views of alternative embodiments of the tubular tip having structural features to permit easy interchangeability and interface with a distal end of the suction tube.

FIG. 24c is a cross-section view of an alternative embodiment of the invention.

FIG. 24d is a bottom view of an alternative embodiment of the invention.

FIG. 25e is a cross-section top view of an alternative embodiment of the invention with an alternative second stylet.

FIG. 25f is a cross-section top view of an alternative embodiment of the invention with an alternative second stylet.

DETAILED DESCRIPTION

Figure 1A:
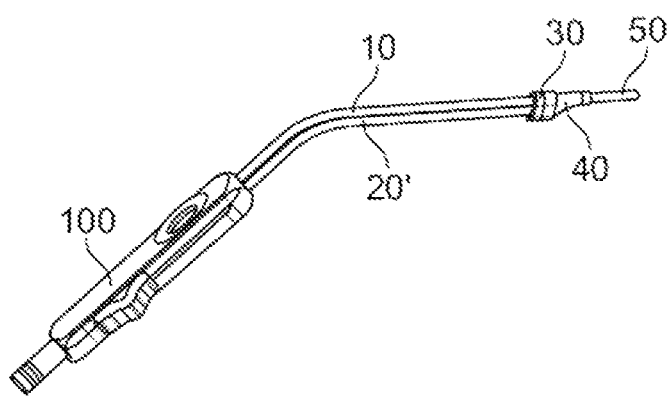
FIG. 1a is a perspective view of one embodiment of the self-cleaning surgical suction device.

To address these problems arising from frequently clogged surgical suction devices, the invention claimed herein enables the surgeon alone to remove obstructions at the distal tip of the surgical suction device. This invention thus bypasses the need for an assistant who, under sterile conditions, is handed a clogged surgical suction device, then manually replaces or unclogs the tip, and hands the surgical suction device back to the surgeon. The invention described herein also functions seamlessly with suction tips of various shapes, thus providing a surgeon with a choice of tip shapes suitable to the application.

In a first embodiment, the invention described herein includes: (a) a suction tube having a first longitudinal axis, a proximal opening, and a distal opening; (b) a guide structure having a second longitudinal axis that is substantially parallel to the first longitudinal axis, a proximal opening, and a distal opening; (c) a stylet having a proximal end and a distal end; and (d) a junction conduit having a proximal opening and a distal opening; wherein, the stylet is disposed along the second longitudinal axis and encircled by the guide structure, and the proximal opening of the junction conduit is in contact with at least the distal opening of the suction tube such that the distal opening of the junction conduit is in fluid communication with the suction tube. Urging the stylet through the guide structure along the second longitudinal axis through the junction conduit translates the distal end of the stylet to the distal opening of the junction conduit.

In a second embodiment, the invention further includes a knob that is fixed at or about the proximal end of the stylet; and/or a tubular base member having a proximal vacuum connector, an intermediate region, and a distal attachment region that are each in fluid communication with one another, wherein the distal attachment region is in contact with the proximal opening of the suction tube such that the proximal vacuum connector is in fluid communication with the suction tube. The tubular base member can include a vent feature disposed on the intermediate region of the tubular base member that is in fluid communication with a vacuum source connected to the vacuum connector at the proximal end of the tubular base member. The vent can control the negative pressure exhibited at the site of the surgical field by the degree to which it is obstructed. To facilitate the degree of obstruction to the vent, the tubular base member includes a vent-surrounding member disposed on the intermediate region. The vent also acts as a muffler to reduce sound created by the flow of air.

In a third embodiment, a receiving member disposed at the distal attachment region encircles the stylet and is coaxial with the guide structure along the second longitudinal axis.

A fourth embodiment includes a handle member that is operably attached to and surrounds the intermediate region and distal attachment region and includes a track element extending substantially parallel to the second longitudinal axis that is proximate to the distal attachment region. A vent-access opening can also be included and disposed such that the vent and vent-surrounding member are accessible through the vent-access opening.

A fifth embodiment includes a tubular tip that contacts and is in fluid communication with the junction conduit.

For convenience of use, in some embodiments the suction tube is bent between the proximal end and distal end. When the suction tube is employed in a bent configuration, the guide structure may also be bent between the proximal end and distal end.

To stabilize the position of the guide structure, the receiving member is in contact with the proximal opening of the guide structure, and a bracket may be disposed proximate to the distal end of the suction tube and proximate to the distal end of the guide structure to conjoin the suction tube and guide structure.

The invention may have a guide structure that is a guide tube that is substantially parallel to and coextensive with the suction tube.

In some cases the guide structure is a shortened guide tube that is substantially parallel to the suction tube, and yet in other cases the guide structure is at least one annulus disposed on the suction tube.

In a sixth embodiment the suction device includes: (a) a suction tube having a first longitudinal axis, a proximal opening, a distal opening, and an entry port disposed proximate to the distal opening; (b) a guide structure having a second longitudinal axis that is substantially parallel to the first longitudinal axis, a proximal opening, and a distal opening; and (c) a hooked stylet having a proximal end and a hooked distal end; wherein, the stylet is disposed substantially along the second longitudinal axis and encircled by the guide structure such that the hooked distal end is disposed in or proximate to the entry port. As the hooked stylet is urged in the distal direction substantially along the second longitudinal axis and through the guide structure, the curvature of the hooked distal end meeting resistance from the distal edge of the entry port translates the hooked stylet into the suction tube and to the distal opening of the suction tube.

In a seventh embodiment, the invention further includes a knob that is fixed at or about the proximal end of the stylet; and/or a tubular base member having a proximal vacuum connector, an intermediate region, and a distal attachment region that are each in fluid communication with one another, wherein the distal attachment region is in contact with the proximal opening of the suction tube such that the proximal vacuum connector is in fluid communication with the suction tube. The tubular base member can include a vent feature disposed on the intermediate region of the tubular base member that is in fluid communication with a vacuum source connected to the vacuum connector at the proximal end of the tubular base member. The vent can control the negative pressure exhibited at the site of the surgical field by the degree to which it is obstructed. To facilitate the degree of obstruction to the vent, the tubular base member includes a vent-surrounding member disposed on the intermediate region. The vent also acts as a muffler to reduce sound created by the flow of air.

In an eighth embodiment, a receiving member disposed at the distal attachment region encircles the stylet and is coaxial with the guide structure along the second longitudinal axis.

A ninth embodiment includes a handle member that is operably attached to and surrounds the intermediate region and distal attachment region and includes a track element extending substantially parallel to the second longitudinal axis that is proximate to the distal attachment region. A vent-access opening can also be included and disposed such that the vent and vent-surrounding member are accessible through the vent-access opening.

For convenience of use, in some embodiments the suction tube is bent between the proximal end and distal end. When the suction tube is employed in a bent configuration, the guide structure may also be bent between the proximal end and distal end.

To stabilize the position of the guide structure, the receiving member is in contact with the proximal opening of the guide structure, and a bracket may be disposed proximate to the distal end of the suction tube and proximate to the distal end of the guide structure to conjoin the suction tube and guide structure.

The invention may have a guide structure that is a shortened guide tube that is substantially parallel to the suction tube, and yet in other cases the guide structure is at least one annulus disposed on the suction tube.

A tenth embodiment of the suction device includes: (a) a suction tube having a first longitudinal axis, a proximal opening, a distal opening, and an entry port disposed proximate to the distal opening; (b) a guide structure having a second longitudinal axis, a proximal opening, and a distal opening; and (c) a stylet having a proximal end and a distal end; wherein, the stylet is disposed substantially along the second longitudinal axis and encircled by the guide structure, and the distal opening of the guide structure is in contact with the entry port of the suction tube and in fluid communication with the distal opening. Urging the stylet through the guide structure substantially along the second longitudinal axis translates the distal end of the stylet through the entry port of the suction tube to the distal opening of the suction tube.

In an eleventh embodiment, the invention further includes a knob that is fixed at or about the proximal end of the stylet; and/or a tubular base member having a proximal vacuum connector, an intermediate region, and a distal attachment region that are each in fluid communication with one another, wherein the distal attachment region is in contact with the proximal opening of the suction tube such that the proximal vacuum connector is in fluid communication with the suction tube. The tubular base member can include a vent feature disposed on the intermediate region of the tubular base member that is in fluid communication with a vacuum source connected to the vacuum connector at the proximal end of the tubular base member. The vent can control the negative pressure exhibited at the site of the surgical field by the degree to which it is obstructed. To facilitate the degree of obstruction to the vent, the tubular base member includes a vent-surrounding member disposed on the intermediate region. The vent also acts as a muffler to reduce sound created by the flow of air.

In a twelfth embodiment, a receiving member disposed at the distal attachment region encircles the stylet and is coaxial with the guide structure along the second longitudinal axis.

A thirteenth embodiment includes a handle member that is operably attached to and surrounds the intermediate region and distal attachment region and includes a track element extending substantially parallel to the second longitudinal axis that is proximate to the distal attachment region. A vent-access opening can also be included and disposed such that the vent and vent-surrounding member are accessible through the vent-access opening.

In a fourteenth embodiment, the guide structure is an alternative guide tube wherein the suction tube and alternative guide tube are bent between their respective proximal and distal ends such that the suction tube and guide structure are substantially parallel until the distal opening of the alternative guide tube connects with the entry port on the suction tube.

In a fifteenth embodiment, the suction device includes: (a) a suction tube having a first longitudinal axis, a proximal opening, a distal opening, and an entry port disposed proximate to the distal opening; (b) a guide structure having a second longitudinal axis that is substantially parallel to the first longitudinal axis, a proximal opening, and a distal opening; (c) a stylet having a proximal end and a distal end; and (d) a lip disposed about the distal end of the entry port; wherein, the stylet is disposed along the second longitudinal axis and encircled by the guide structure, and as the stylet is urged through the guide structure along the second longitudinal axis the distal end of the stylet moves along the curvature or slope of the lip and is translated through the entry port to the distal opening of the suction tube.

In a sixteenth embodiment, the invention further includes a knob that is fixed at or about the proximal end of the stylet; and/or a tubular base member having a proximal vacuum connector, an intermediate region, and a distal attachment region that are each in fluid communication with one another, wherein the distal attachment region is in contact with the proximal opening of the suction tube such that the proximal vacuum connector is in fluid communication with the suction tube. The tubular base member can include a vent feature disposed on the intermediate region of the tubular base member that is in fluid communication with a vacuum source connected to the vacuum connector at the proximal end of the tubular base member. The vent can control the negative pressure exhibited at the site of the surgical field by the degree to which it is obstructed. To facilitate the degree of obstruction to the vent, the tubular base member includes a vent-surrounding member disposed on the intermediate region. The vent also acts as a muffler to reduce sound created by the flow of air.

In a seventeenth embodiment, a receiving member disposed at the distal attachment region encircles the stylet and is coaxial with the guide structure along the second longitudinal axis.

An eighteenth embodiment includes a handle member that is operably attached to and surrounds the intermediate region and distal attachment region and includes a track element extending substantially parallel to the second longitudinal axis that is proximate to the distal attachment region. A vent-access opening can also be included and disposed such that the vent and vent-surrounding member are accessible through the vent-access opening.

For convenience of use, in some embodiments the suction tube is bent between the proximal end and distal end. When the suction tube is employed in a bent configuration, the guide structure may also be bent between the proximal end and distal end.

To stabilize the position of the guide structure, the receiving member is in contact with the proximal opening of the guide structure, and a bracket may be disposed proximate to the distal end of the suction tube and proximate to the distal end of the guide structure to conjoin the suction tube and guide structure.

The invention may have a guide structure that is a shortened guide tube that is substantially parallel to the suction tube, and yet in other cases the guide structure is at least one annulus disposed on the suction tube.

A nineteenth embodiment includes a suction device generally comprising: a suction tube having a first longitudinal axis, a proximal opening, a distal opening, and a suction lumen disposed therebetween; a guide structure having a first guide lumen and a second guide lumen, wherein the first guide lumen is coaxial with the suction lumen; a stylet having a proximal end and a distal end, wherein the stylet is coaxially disposed within the second guide lumen; and a junction point intersecting the distal opening of the first guide lumen and the distal opening of the second guide lumen, and axial movement of the stylet through the second guide lumen along the second longitudinal axis through the junction point translates the distal end of the stylet into the suction lumen.

Figure 1B:
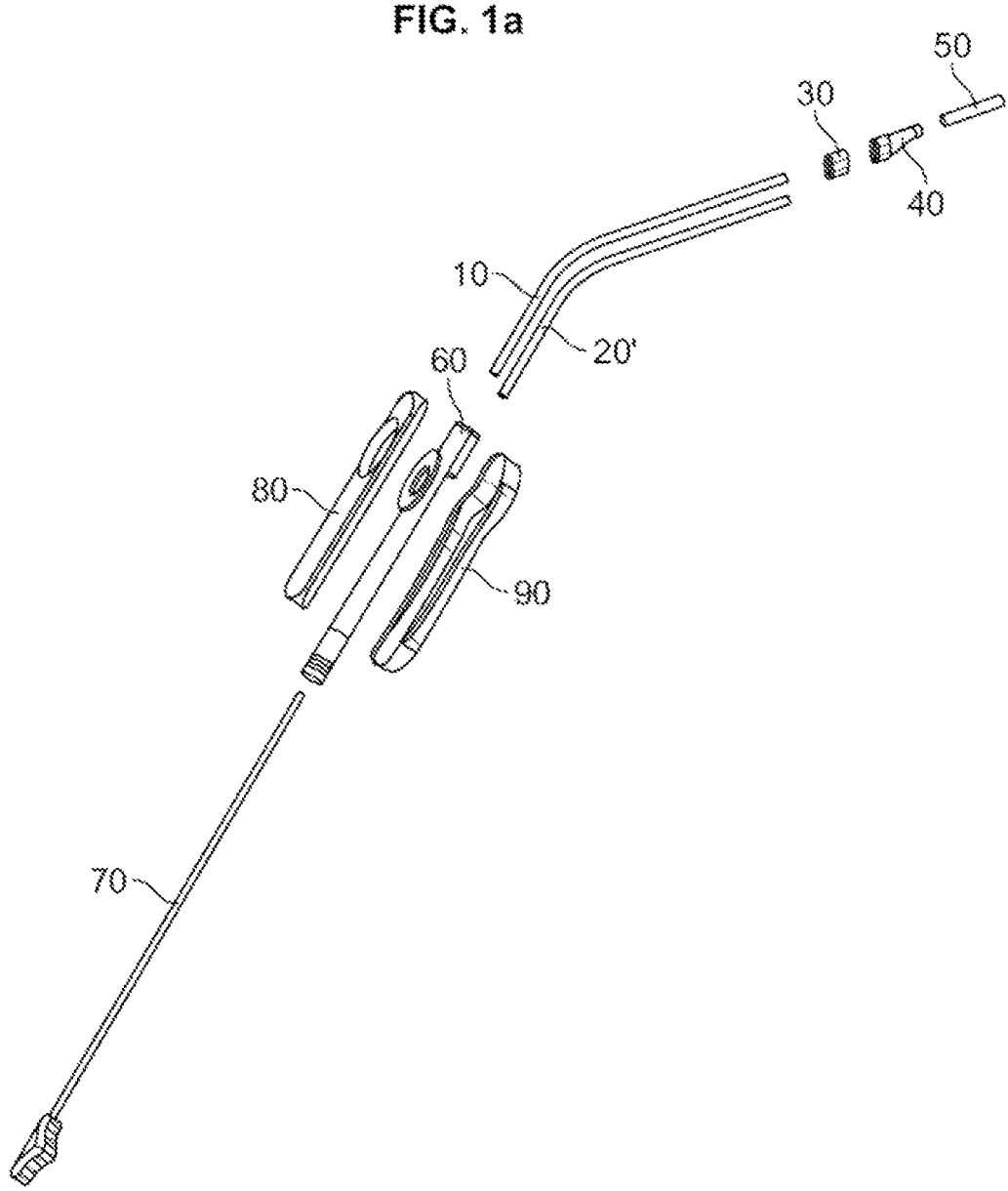

As shown in FIGS. 1a and 1b, one embodiment of a self-cleaning surgical suction device 1 comprises a suction tube 10, a guide structure 20, a bracket 30, a junction conduit 40, a tubular tip 50, a base member 60, a stylet 70, and a handle member 100; wherein, the guide structure 20 is in the form of a guide tube 20'.

In one embodiment of the self-cleaning surgical suction device 1, the suction tube 10 and guide tube 20' are substantially parallel to and coextensive with each other. As shown in FIG. 2a, the suction tube 10 includes a first longitudinal axis 12, a proximal opening 14, and a distal opening 16. In the depicted embodiment, the suction tube 10 measures about five inches to about six inches in length with an inner diameter of about five-hundredths of an inch to about a tenth of an inch and an outer diameter of about a tenth of an inch to about fifteen hundredths of an inch. Other embodiments of the present invention include a suction tube 10 that is substantially shorter or longer, having inner diameters and outer diameters that are substantially smaller or larger as befits the intended use. For example, a veterinarian about to surgically remove debris from a laceration in a large animal, appropriately sedated, would be better served using a larger surgical suction device 1; whereas, a dentist needing to sculpt a tooth in a young child would find a smaller such device more serviceable. Accordingly, the dimensions presented for the suction tube, as well as other components of the present invention, are merely examples of the various described embodiments of the present invention and are by no means to be considered limiting.

FIG. 3a illustrates the guide tube 20' which includes a second longitudinal axis 22, a proximal opening 24 and a distal opening 26. The guide tube 20' measures about five inches to about six inches in length with an inner diameter of about five-hundredths of an inch to about a tenth of an inch and an outer diameter of about a tenth of an inch to about fifteen-hundredths of an inch.

The suction tube 10 and guide tube 20' may be made from materials such as any of the following, without limitation intended: (a) metals, such as stainless steel, aluminum, and other suitable metals or alloys thereof; (b) polymers, such as polyvinylchloride, nylon, polytetrafluoroethylene, polystyrene, acrylonitrile-butadiene styrene, polypropylene, and other suitable plastics; or (c) ceramics, such as silicon carbide, tungsten carbide, apatite, and other suitable ceramics; wherein the suitable metals, alloys, plastics, or ceramics respectively have a tensile strength sufficient to maintain a tubular structure and are capable of being sterilized for medical use. One of ordinary skill in the art is necessarily familiar with the indicated range of alternative materials that have the identified characteristics associated with their suitability for the identified use.

As shown in FIG. 1, the suction tube 10 and the guide tube 20' may be bent obliquely. Alternatively, the suction tube 10 and the guide tube 20' may be bent to approximate a right angle. In yet other embodiments, the suction tube 10 and the guide tube 20' are not bent.

The suction tube 10 and guide tube 20' may be conjoined by the bracket 30 proximate to the distal opening 16 of the suction tube 10 and the distal opening 26 of the guide tube 20', as illustrated by the completed assembly in FIG. 1a. The bracket 30 may be disposed at the distal end of the suction tube 10 and guide tube 20' by overmolding, frictional attachment, welding, and/or glued around the suction tube 10 and guide tube 20'. In one embodiment, the bracket is overmolded and glued around the suction tube 10 and guide tube 20'. As shown in FIG. 4, a small length of the suction tube 10 extends beyond the distal end of the bracket 30. In other embodiments a small length of both the suction tube 10 and guide tube 20' may extend beyond the distal end of the bracket 30 or a small length of the guide tube 20' may extend beyond the distal end of the bracket 30.

The distal opening 16 of suction tube 10 extending beyond the distal end of the bracket 30 is in contact with a junction conduit 40 by way of inserting the distal end of the suction tube 10 extending beyond the distal end of the bracket 30 into a proximal opening 42 of the junction conduit 40 and set by a suitable adhesive, e.g., a cyanoacrylate adhesive, such as Loctite 4011™ or 4161™ Prism® manufactured by Henkel, such that a distal opening 44 of the junction conduit 40 is substantially coaxial with the suction tube 10 along first longitudinal axis 12, and in fluid communication with the suction tube 10.

In alternative embodiments, the distal opening 44 of the junction conduit 40 is not coaxial with the suction tube 10 along the first longitudinal axis 12. The proximal opening 42, as shown in FIG. 5b, has an elliptical shape with an inner minor axis length 43 ranging from about a tenth of an inch to about fifteen-hundredths of an inch. The junction conduit 40 may alternatively be set by welding. The junction conduit 40 may also be set by frictional attachment enabling disengagement of the junction conduit 40 from the suction tube 10.

The bracket 30 and junction conduit 40 may be made from materials such as any of the following, without limitation intended: (a) metals, such as stainless steel, aluminum, and other suitable metals or alloys thereof; (b) polymers, such as polyvinylchloride, nylon, polytetrafluoroethylene, polystyrene, acrylonitrile-butadiene styrene, polypropylene, and other suitable plastics; or (c) ceramics, such as silicon carbide, tungsten carbide, apatite, and other suitable ceramics; wherein the suitable metals, alloys, plastics, or ceramics respectively have a tensile strength sufficient to maintain the intended structure and are capable of being sterilized for medical use. One of ordinary skill in the art is necessarily familiar with the indicated range of alternative materials that have the identified characteristics associated with their suitability for the identified use.

As shown in FIG. 1, a tubular tip 50 may be in contact with the junction conduit 40. FIG. 6 illustrates that the tubular tip 50 has a proximal opening 52 and distal opening 54. The tubular tip 50 may be made of metals, alloys, polymers, or ceramics as mentioned above for alternative materials for the suction tube 10 and the guide tube 20. It may be shaped as shown in FIG. 6 as a regular cylinder having the same diameter at its proximal opening 52 as at its distal opening 54, or it may be shaped having a narrower distal opening versus its proximal opening such that the negative pressure of the suction is increased at the business end of the suction device allowing the user to direct the suction more particularly for removing fluids and/or particulates from a surgical field. In yet another embodiment, the narrower opening can be at the proximal opening allowing the distal opening to address a larger area for removing a large quantity of fluids and/or particulates. These alternatives tubular tips are described further below.

In the embodiment that is depicted in FIG. 6, the outer and inner diameters of the tubular tip 50 are constant throughout the component, thus describing a regular cylinder having any suitable diameter usefully employed for removing fluids and/or particulates that accumulate in a surgical field, for example. Using the French (Fr) scale of measurement for outer diameters of medical tubing or catheters, where each increment of measurement represents 0.33 mm such that a 3 Fr tube has an outer diameter of 1 mm, tubular tips of the present invention, in one embodiment, have a proximal opening 52 and distal opening 54 that each measure about 9 Fr, about 12 Fr, about 15 Fr, or about 18 Fr. In this same embodiment, the outer dimension of the suction tube 10 is also respectively about 9 Fr, about 12 Fr, about 15 Fr, or about 18 Fr. The inner diameter of the suction tube 10 and the tubular tip 50 of this embodiment can be the same or can vary there between, but is generally about one-half to one millimeter less relative to the outer diameter, depending on the thickness of the material used for the wall and manufacturing tolerances. Accordingly, the inner diameters range between about 2 and 2.5 mm, about 3 and 3.5 mm, about 4 and 4.5 mm, and about 5 and 5.5 mm with regard to each of the respective exemplary sizes of tubular tips set forth above.

As noted above, neither the outer diameter nor the inner diameter of the tubular tip is necessarily constant, i.e., the diameters may or may not be uniform. Moreover, in view of the use of the suction device for removal of debris and/or fluids from a surgical field, the overall size of the device is not critical and it should be understood that the device is described with reference to measuring conventions employed for medical tubing and catheters as a convenience and not because there are necessarily narrow tolerances and requirements for appropriate use of the inventive device. Accordingly, when stating that a tubular tip has an outer diameter of 12 Fr, it is plainly the case that one skilled in the art would fully appreciate that a second device having a tubular tip that is as much as 25% less in diameter or 33% greater in diameter would be capable of serving the equivalent function in the same manner.

As to non-uniform outer diameters of the tubular tip, in one embodiment, for example, as shown in FIG. 21, the tubular tip 50' or 50" describe a funnel shape when viewing it from its point of attachment to the junction conduit 40 at its proximal opening 52a or 52b to the distal opening Ma or 54b, respectively, where it has a lesser diameter relative to the proximal opening 52. The funnel shape may involve a gradual narrowing of the tubular tip from proximal opening to distal opening as shown in tubular tip 50'; alternatively, in another embodiment, the funnel shape may include a rapid narrowing of the tubular tip in the same direction as shown in tubular tip 50". The point along the tubular tip that it begins to narrow can start at any point as long as the dimensions and shape of the proximal opening 52a or 52b meshes with the opening 44 of the junction conduit as, for example, shown in FIG. 5c. As will be further described below, there are alternative mechanisms available for attaching the tubular tip to the junction conduit, so the precisely depicted insertion method of the junction conduit shown in FIG. 5c is not limiting on the diameter requirements of the proximal opening 52 for a given tubular tip. However, the proximal opening is necessarily designed to mesh with the junction conduit and the attaching mechanism that is employed, of which alternatives are presented below. Accordingly, with the sole exception of the requirements for the point of attachment between the distal opening of the junction conduit 40 and the proximal opening 52 of the tubular tip, the narrowing of the tubular tip can begin at any point along the length of the tubular tip 50' or 50".

In one embodiment having funnel-shaped tubular tips 50' or 50", the proximal opening 52a or 52b is, for example, about 18 Fr and a series of tubular tips are provided that have distal openings 54a or 54b, respectively, that are about 16 Fr, about 14 Fr, about 12 Fr, about 10 Fr, and/or about 8 Fr, and which are interchangeably employed on the suction device. In a second embodiment having funnel-shaped tubular tips 50' or 50", the proximal opening 52a or 52b is, for example, about 15 Fr and a series of tubular tips are provided that have distal openings Ma or 54b, respectively, that are about 14 Fr, about 12 Fr, about 10 Fr, and/or about 8 Fr, and which are interchangeably employed on the suction device. In a third embodiment having funnel-shaped tubular tips 50' or 50", the proximal end 52a or 52b is, for example, about 12 Fr and a series of tubular tips are provided that have distal openings Ma or 54b, respectively, that are about 11 Fr, about 10 Fr, about 9 Fr, and/or about 8 Fr, and which are interchangeably employed on the suction device.

An inverse funnel shape for the tubular tips can be usefully employed in the context of the present invention as well, so that a larger area of the surgical field can be addressed by the suction device at the same time. As shown in FIG. 21 with respect to tubular tip 50''' or 50'''', the proximal opening 52c or 52d is narrower than the distal opening 54c or 54d, respectively. Analogously to the funnel shaped tubular tips described above, the inverse-funnel shaped tubular tips may involve a gradual broadening of the tubular tip from proximal opening to distal opening as shown in tubular tip 50'''; alternatively, in another embodiment, the inverse funnel shape may include a rapid broadening of the tubular tip in the same direction, as shown in tubular tip 50''''. The point along the tubular tip that its cross-sectional dimensional starts increasing, as in the funnel-shape tubular tips described above, can be at any point so long as the mechanism for attachment of the tubular tip to the junction conduit is accommodated. Accordingly, for a friction-based mechanism where the proximal opening 52 of the tubular tip 50 slides into the distal opening 44 of the junction conduit 40, the outer diameter of the tubular tip at the proximal opening thereof must snugly fit into the distal opening 44 of the junction conduit. The outer diameter of the tubular tip can commence increasing at any point distal to the point attachment between the tubular tip and the junction conduit.

The operator of the suction device elects which suction tip to use, where a larger distal opening is preferably employed, perhaps for its ability to lessen the likelihood of clogging and/or for its ability to be gentler to tissue in the surgical field that is intended to remain there (as compared to the smaller distal opening that can exert a higher degree of negative pressure from the suction device that may distress healthy tissue); and where a smaller distal opening increases the potential negative pressure, thus plausibly better suited for removing larger quantities of fluids at a faster rate but runs a higher risk of becoming clogged by particulates. The decision of area addressed by the distal opening of the tubular tip may also be influenced if useful to the procedure to treat a larger proportion of the surgical field at a time by a constant level of the negative pressure.

Additional variant tubular tips are also contemplated in the context of the present invention that, for example, have varying lengths for reaching deeper into a cavity in which a surgical field may be disposed. The tubular tips can be manufactured to any length desired, and among lengths viewed to be suitable for the purpose of removing fluid and debris from a surgical field, it is contemplated to set the overall lengths of the tubular tips at between about one centimeter to about 30 cm, inclusive of all such approximate lengths corresponding to each integer there between; wherein the shorter such lengths would have particular utility for surgeries on small animals, such as, for example, a mouse, cat, or small dog, the longer such lengths would have particular utility for surgeries on large animals, such as, for example, cows, horses, or (especially zoo- or aquarium-bound) game animals, and the intermediate lengths would have particular utility for surgeries on humans and other such sized surgery candidates.

Figure 23A:
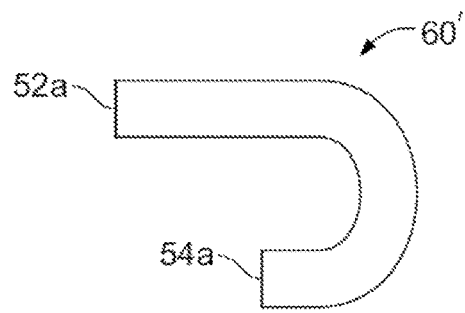
FIGS. 23a-e each show a series of profile views of alternative embodiments of the tubular tip depicting different degrees of bends of the tubular tip along a longitudinal axis thereof.
Figure 23B:
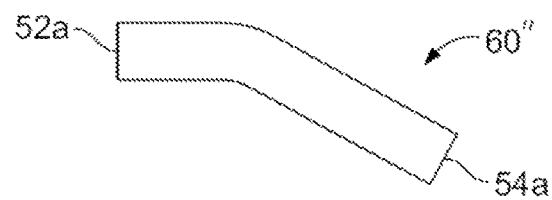
Figure 23C:
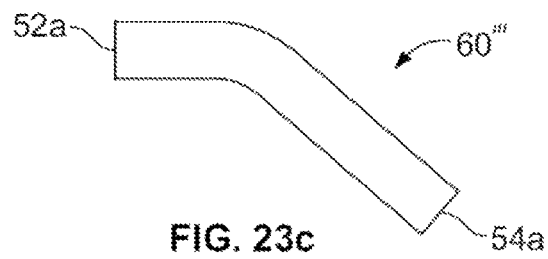
Figure 23D:
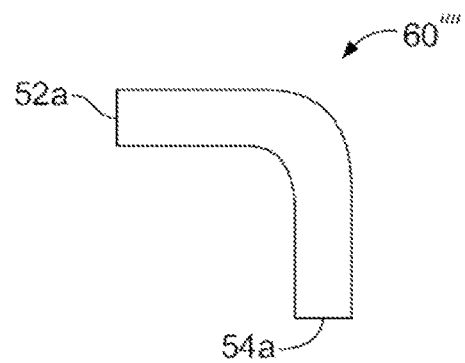
Figure 23E:
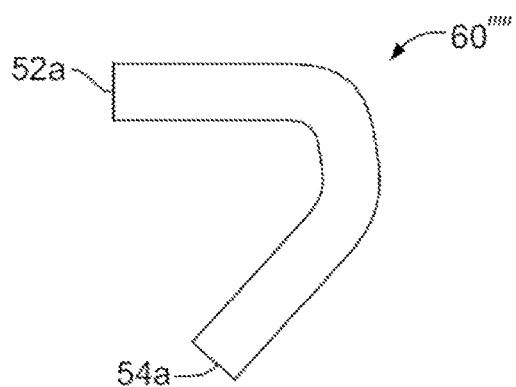

Other embodiments of alternative tubular tips include those that have bends in the tube, which bends can be set to any degree relative to the longitudinal axis of the tubular tip. Addressing this aspect of the present invention with practical examples, usefully employable bent tubular tips 60', 60", 60''', 60'''' and 60''''' depicted in FIGS. 23a-e, respectively, include those that indeed double back about 180° (FIG. 23a) as well as those having about a 30° bend (FIG. 23b) or about a 45° bend (FIG. 23c) or about a 90° bend (FIG. 23d) or about a 135° bend (FIG. 23e), which bent tubular tips allow for easier treatment of, as one non-limiting example, surfaces that are, again, in a cavity and on the sides thereof, or under a component protruding into the cavity of the surgical field, or under a layer of skin at or about the opening of the surgical field. It will be understood that in accordance with these alternative embodiments of the tubular tips, the bend may be preset during manufacture of the tubular tip or, alternatively, the tubular tip may be made of a plastically or mechanically deformable material such that it is bendable by the user to any desired angle relative to the longitudinal axis of the tubular tip.

The suction device of the present invention having a multiplicity of interchangeable tubular tips that can be employed provides a number of advantages over prior art suction devices where the tip could not be removed. If, for example, a tubular tip becomes clogged to an extent that even the unclogging mechanism of the present invention is not fully effective, then the surgeon or other user (such as an operating room nurse) can simply remove the clogged tubular tip and replace it with a new one, resulting in a faster solution than having to replace the entire suction device and likely halt or delay the surgery. Being disposable, the interchangeable tips upon being exchanged out do not suffer the defect of prior art "reusable" suction tips that inevitably accumulate old blood. Moreover, the disposable, interchangeable suction tips are more cost effective in providing multiples of the same-sized suction tips and/or different-sized suction tips in the same package.

In one embodiment, the tubular tip 50 is in contact with the junction conduit 40 by way of inserting the proximal end of the tubular tip 50 through the distal opening 44 of the junction conduit 40 and set by a suitable adhesive, e.g., a cyanoacrylate adhesive, such as Loctite® 4011™ or 4161™ Prism manufactured by Henkel, such that the tubular tip 50 is coaxial with the suction tube 10 along the first longitudinal axis 12, and in fluid communication with the suction tube 10. In alternative embodiments the tubular tip 50 is not coaxial with the suction tube 10 along the first longitudinal axis 12. Suitable adhesives are identified with respect to water-resistant characteristics; if the joining of tubular tip to junction conduit is to be permanent, then the suitable adhesive joins the two components irreversibly, and if the joining is to be reversible, the suitable adhesive does not so attack the materials of the two components such that one can remove the tubular tip from the junction conduit and the suction device can be used with interchangeable tubular tips.

The tubular tip 50 may alternatively be set by welding, which is another joining mechanism suitable for one-time uses of the suction device.

The tubular tip 50 may also be fitted without welding or adhesives enabling disengagement of the tubular tip 50 from the junction conduit 40. For example, the tubular tip 50 may have an outside diameter that is less than the inner diameter of the distal opening 44 of the junction conduit 40 such that the tubular tip 50 can be pushed and/or twisted into the distal opening 44 and held in place by frictional forces. In another example, the proximal end of the tubular tip 50 may be threaded so that it may be twisted into the junction conduit 40 that, again, has a slightly larger inner diameter relative to the outer diameter of the proximal end 52 or, in yet another embodiment, corresponding threads disposed proximate to the inner diameter of the distal opening 44 of the junction conduit 40 are employed.

Disengageable joining of the tubular tip 50 to the junction conduit 40 as described above involves a "twist-on" or "screw-on" method of attachment there between. Irrespective whether or not threads are employed (i) on the inner surface of the junction conduit 40 without corresponding threads on the opposing outer surface of the tubular tip 50, or (ii) on the outer surface of the tubular tip 50 without corresponding threads on the opposing inner surface of the junction conduit 40, or (iii) with corresponding threads on each of said surfaces, or (iv) without threads on either of said surfaces, as each such possible employment of threads are described in the immediately prior paragraph, one can invoke frictional forces and attach a particular tubular tip 50 to an appropriately sized junction conduit 40 using a twist-on or screw-on movement of one of the identified components relative to the other.

It is also the case, in another embodiment, that the identified components are sized such that the proximal opening 52 of the tubular tip 50 fits over the distal opening 44 of the junction conduit 40, but snugly so. In that case, whether or not threads are employed (i) on the outer surface of the junction conduit 40 without corresponding threads on the opposing inner surface of the tubular tip 50, or (ii) on the inner surface of the tubular tip 50 without corresponding threads on the opposing outer surface of the junction conduit 40, or (iii) with corresponding threads on each of said surfaces, or (iv) without threads on either of said surfaces, one can invoke frictional forces and attach a particular tubular tip 50 to an appropriately sized junction conduit 40, wherein the inner diameter of the tubular tip 50 at its proximal opening is slightly larger than the outer diameter of the distal opening of junction conduit 40, the precision of which can be readily determined by one skilled in the art of joining tubular members, as in, for example, a cap for closing a bottle top or joining one laboratory hose to another.

Such a joining action of the tubular tip 50 to an appropriately sized junction conduit 40, irrespective whether the proximal opening of the tubular tip 50 fits about or into the distal opening of the junction conduit 40, and, as well, irrespective whether all opposing surfaces are manufactured with meshing threads or only one of the opposing surfaces includes threads or neither of the surfaces includes threads, involves a "screw-on" or "twist-on" or "push-on" action of one component relative to the other for the attachment of the indicated components.

In yet another embodiment, using a bayonet fitting, the proximal end of the tubular tip 50 as shown in FIG. 22a has a protruding pin 51 at a point on its outer surface that fits into a channel located on the inner surface of the distal opening 44 (channel not shown), where the channel runs straight into the junction conduit 40 for a short distance, such as, without limitation, about 2-3 mm, and then runs another short distance orthogonally thereto so as to lock the tubular tip 50 in place. One could alternatively include two or three such protruding pins and an equal number of such channels for securing the tubular tip to the junction conduit (neither additional pins nor channels are shown). Instead of a channel in which to insert the protruding pin(s), one could engineer the inner surface of the distal opening 44 with a circumferential ridge (not shown) over which the protruding pin(s) could be pushed and thus hold the tubular tip in place thereby. The opposite approach could also work to secure the tubular tip, where a circumferential ridge 53 is placed on the outer surface of a tubular tip toward its proximal opening 52, as shown on FIG. 22b; in which case, the inner surface of the distal opening 44 of the junction conduit 40 has one or more protruding pins (not shown) or a circumferential ridge, and the tubular tip then "snaps" into place by being pushed such that the protruding aspects of the tubular tip 50 and the distal opening 44 of the junction conduit 40 slide past one another.

In yet another embodiment for a joining mechanism for using the interchangeable tubular tips, the tubular tips can be made with a depression 55 on its outer surface close to the proximal opening thereof, as shown, for example, in FIG. 22c, and the depression is then pushed to engage and remain in contact with a protruding pin or one of a multiplicity of protruding pins located on the inner surface of the inner surface of the distal opening 44 of the junction conduit 40 (protruding pin(s) not shown). One could as readily reverse the locations for the protruding pins and depressions with respect to the junction conduit and the tubular tip. As yet one more embodiment for a mechanism for the easy attachment and removal of the tubular tips of the present invention onto the suction device, instead of a "point" of depression for engagement with a protruding pin, one of the two meeting surfaces (i.e., the outer surface of the proximal opening of the tubular tip and the inner surface of the distal opening of the junction conduit) can instead have a circumferential depression 57 (with respect to the tubular tip 50, as an example) that rings one of the two surfaces and either a series of protruding points or a circumferential ridge that meshes with the area of depression.

Another embodiment involves one or more pins or a protruding line (as, for example, the circumferential ridge 53 of FIG. 22b) of material on the outer surface of the tubular tip 50 that, when inserted into the junction conduit 40 and passes a corresponding protruding line manufactured into the inner surface of the junction conduit, creates a "snapping" sound as the tubular tip 50 "snaps" into place. These and other mechanisms for interchangeable insertion of the tubular tip 50 into the junction conduit 40 allow for rapid change of the business end of the suction device, thus allowing a surgeon to change the size or shape of the tip that is usefully employed.

Figure 7A:
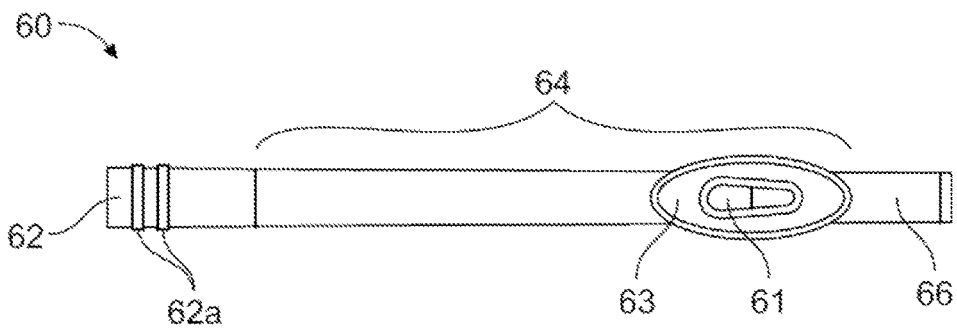
FIG. 7a is a top view of the tubular base member.

As shown in FIG. 1, an embodiment of a self-cleaning surgical suction device 1 also comprises a tubular base member 60. FIG. 7a shows that the tubular base member 60 comprises a proximal vacuum connector 62, an intermediate region 64, a distal attachment region 66, and a distal attachment opening 67 that is in fluid communication with the proximal vacuum connector 62. The tubular base 60 may be made from materials such as any of the following, without limitation intended: (a) metals, such as stainless steel, aluminum, and other suitable metals or alloys thereof; (b) polymers, such as polyvinylchloride, nylon, polytetrafluoroethylene, polystyrene, acrylonitrile-butadiene styrene, polypropylene, and other suitable plastics; or (c) ceramics, such as silicon carbide, tungsten carbide, apatite, and other suitable ceramics; wherein the suitable metals, alloys, plastics, or ceramics respectively have a tensile strength sufficient to maintain the intended structure and are capable of being sterilized for medical use. One of ordinary skill in the art is necessarily familiar with the indicated range of alternative materials that have the identified characteristics associated with their suitability for the identified use. In one embodiment, the tubular base 60 is made of acrylonitrile-butadiene styrene.

The proximal end of the suction tube 10 is inserted into the distal attachment region 66 through the distal attachment opening 67 such that the suction tube 10 is in fluid communication with the proximal vacuum connector 62. The suction tube 10 is set within the distal attachment region 66 by welding or adhesives such that the tubular base member 60 is coaxial with the suction tube 10 along the first longitudinal axis 12. In one embodiment, the suction tube 10 is set within the distal attachment region 66 by a suitable adhesive, e.g., a cyanoacrylate adhesive, such as Loctite 4011 or 4161 Prism manufactured by Henkel. Alternative embodiments not shown include a connection such that the distal attachment region 66 is set within the suction tube 10 by welding or adhesives such that the suction tube 10 is coaxial with the tubular base member 60.

Figure 7B:
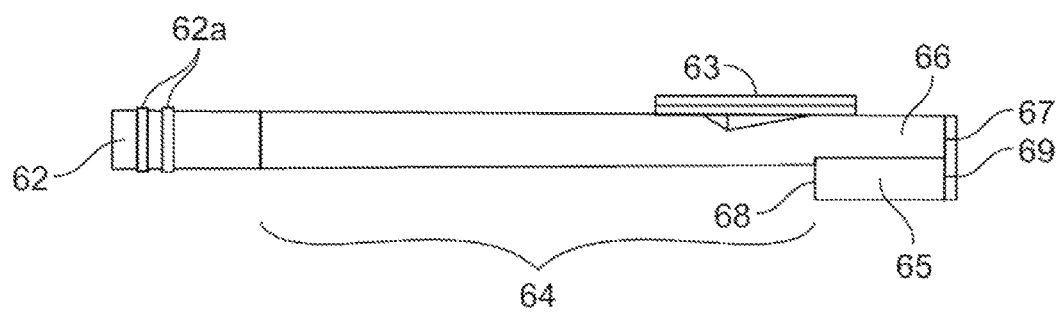
FIG. 7b is a profile view of the tubular base member.
Figure 7C:
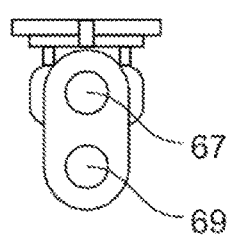
FIG. 7c is frontal view of the distal end of the tubular base member.

As shown in FIG. 7b, the tubular base member 60 also comprises a receiving member 65, a proximal receiving member opening 68, and a distal receiving member opening 69. The receiving member 65 may be disposed on the distal attachment region 66 by welding, gluing, or may be part of a monolithic mold or cast of the tubular base member 60. In one embodiment, the receiving member 65 is tubular and disposed on the distal attachment region 66 as part of a monolithic molding of the tubular base member 60 such that the receiving member 65 is substantially parallel to the distal attachment region 66.

The proximal opening 24 of the guide tube 20 is in contact with the receiving member 65 by way of inserting the proximal end of the guide tube 20 into the receiving member 65 through the distal receiving member opening 69. The guide tube 20 may be set within the receiving member 65 by welding or adhesives such that the receiving member 65 is coaxial with the guide tube 20 along the second longitudinal axis 22. In one embodiment, the guide tube 20 is set within the receiving member 65 by a suitable adhesive, e.g., a cyanoacrylate adhesive, such as Loctite 4011 or 4161 Prism manufactured by Henkel. Alternative embodiments not shown include a connection such that the receiving member 65 is set within the guide tube 20 by welding or adhesives such that the receiving member 65 is coaxial with the guide tube 20 along the second longitudinal axis 22.

The proximal vacuum connector 62 may or may not have external threads 62a facilitating firm attachment of vacuum tubing (not shown) to the vacuum connector 62.

A vent 61, as shown in FIG. 7a, is disposed on the intermediate region 64 of the tubular base member 60 and is in fluid communication with the proximal vacuum connector 62 and the distal opening 54 of the tubular tip 50. The vent 61 can act as a muffler by decreasing the noise from rapid air flow. The vent 61 can also control the amount of negative pressure at the distal opening 54 of the tubular tip 50 by varying the amount the vent 61 is obstructed.

A vent-surrounding member 63 surrounds the vent 61 and facilitates manual control of the degree of obstruction. The vent-surrounding member 63 may be made from materials such as any of the following, without limitation intended: (a) metals, such as stainless steel, aluminum, and other suitable metals or alloys thereof; (b) polymers, such as polyvinylchloride, nylon, polytetrafluoroethylene, polystyrene, acrylonitrile-butadiene styrene, polypropylene, and other suitable plastics; or (c) ceramics, such as silicon carbide, tungsten carbide, apatite, and other suitable ceramics; wherein the suitable metals, alloys, plastics, or ceramics respectively have a tensile strength sufficient to maintain the intended structure and are capable of being sterilized for medical use. One of ordinary skill in the art is necessarily familiar with the indicated range of alternative materials that have the identified characteristics associated with their suitability for the identified use. In one embodiment, the vent-surrounding member 63 is made of acrylonitrile-butadiene styrene.

The vent surrounding member 63 may be welded to the tubular base member 60, glued to the tubular base member 60, or may be part of a monolithic mold or cast of the tubular base member 60. In one embodiment the vent surrounding member 63 is glued on the intermediate region 64 of the tubular base member 60 by a suitable adhesive, e.g., a cyanoacrylate adhesive, such as Loctite 4011 or 4161™ Prism manufactured by Henkel. In one embodiment the vent surrounding member 63 is concave and has an elliptical geometry to further aid in controlling the degree vent 61 is obstructed. Other embodiments may include a rectangular, and/or flat vent surrounding member 63. Another embodiment does not include the vent surrounding member 63.

Figure 8A:
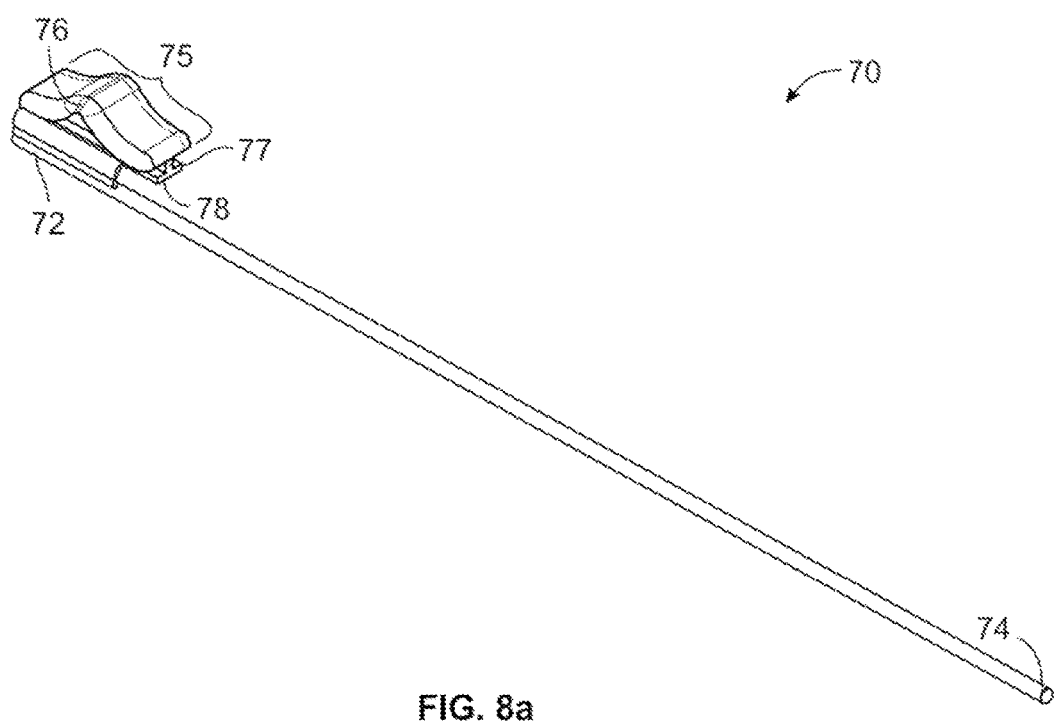
FIG. 8a is a perspective view of the stylet with the attached knob.

A stylet 70 having a proximal end 72 and distal end 74, as shown in FIG. 8a, is disposed within the guide tube 20' by inserting the distal end 74 of the stylet 70 into the proximal receiving member opening 68, through the receiving member 65, out the distal receiving member opening 69, and into the guide tube 20'. The length of stylet 70 ranges from about seven inches to about nine inches. The diameter of the stylet 70 ranges from about five-hundredths of an inch to about a tenth of an inch. The stylet 70 may be made from materials such as any of the following without limitation intended: (a) metals such as stainless steel, aluminum, and other suitable metals or alloys thereof, or (b) polymers such as nylon, polyvinylchloride, polytetrafluoroethylene, polystyrene, acrylonitrile-butadiene styrene, polypropylene, and other suitable plastics; wherein the suitable metals, alloys, or plastics respectively have the suitable elasticity for non-linear movement and can be sterilized for medical use. One of ordinary skill in the art is necessarily familiar with the indicated range of alternative materials that have the identified characteristics associated with their suitability for the identified use. In one embodiment, the stylet is composed of a polymer compound, more particularly, the stylet is composed of nylon, polyvinylchloride, polytetrafluoroethylene, polystyrene, acrylonitrile-butadiene styrene, polypropylene, and other suitable plastics, the suitability of which is a function of sufficient flexibility, stiffness, and ability to be sterilized at least once.

Figure 8B:
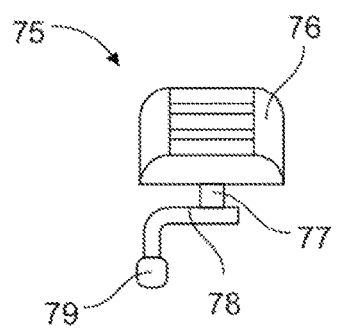
FIG. 8b is a frontal view of the knob.

As shown in FIG. 8b, a knob 75 having a node 76, a web 77, a flange 78, and a grip 79 may be fixed to the stylet 70 by welding, gluing, and/or frictionally attaching the grip 79 to about the proximal end of the stylet 70. In one embodiment the knob 75 is fixed at about the proximal end 72 of the stylet 70 by frictional attachment to the grip 79, and in another embodiment the knob 75 may be located at about the proximal end of the stylet 70 as part of a monolithic mold or cast of the stylet 70. In one embodiment, the knob 75 facilitates manual urging of the stylet 70 in the distal direction through the guide tube 20' along the second longitudinal axis 22 by manually displacing the node 76 in the distal direction. As the distal end 74 of the stylet 70 is urged through the junction conduit 40, the motion of the distal end 74 is translated from the second longitudinal axis 22 to the first longitudinal axis 12 out the distal opening 44 of the junction conduit 40 and through the tubular tip 50. The distal end 74 of the stylet 70 can be retracted by manually displacing the knob 75 by urging the node 76 towards the proximal direction. Negative pressure exhibited at the distal opening 54 of the tubular tip 50 may be varied in proportion to the manual displacement of the knob 75 as the distal end 74 of the stylet 70 coincides with the suction tube 10.

The flange 78 may take an "L" shape with a curved bend as shown from a frontal view for an embodiment of the invention shown in FIG. 8b. The flange 78 may take other shapes such as an "L" shape with a sharp angled bend or any other suitable shape that allows the flange 78 and grip 79 assembly to get around the tubular base member 60.

The knob 75 may be made from materials such as any of the following, without limitation intended: (a) metals, such as stainless steel, aluminum, and other suitable metals or alloys thereof; (b) polymers, such as polyvinylchloride, nylon, polytetrafluoroethylene, polystyrene, acrylonitrile-butadiene styrene, polypropylene, and other suitable plastics; or (c) ceramics, such as silicon carbide, tungsten carbide, apatite, and other suitable ceramics; wherein the suitable metals, alloys, plastics, or ceramics respectively have a tensile strength sufficient to maintain the intended structure and are capable of being sterilized for medical use. One of ordinary skill in the art is necessarily familiar with the indicated range of alternative materials that have the identified characteristics associated with their suitability for the identified use. In one embodiment, the knob 75 is made of acrylonitrile-butadiene styrene.

Figure 9:
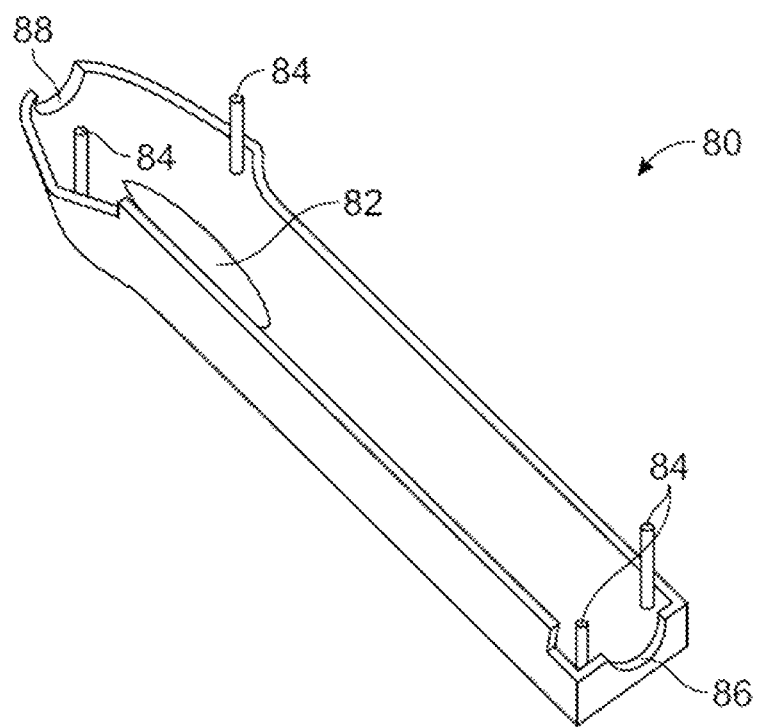
FIG. 9 is a perspective view of the dorsal handle piece.

As shown in FIG. 1, an embodiment also includes a handle member 100 comprising of a dorsal handle piece 80 and a ventral handle piece 90. The dorsal handle piece 80, as shown in FIG. 9, includes a vent-access opening 82, a plurality of interference fit posts 84, a proximal dorsal recess 86, and a distal dorsal recess 88. The dorsal handle piece 80 may be made from materials such as any of the following without limitation intended: (a) metals such as stainless steel, aluminum, and other suitable metals or alloys thereof; (b) polymers such as nylon, polyvinylchloride, polytetrafluoroethylene, polystyrene, acrylonitrile-butadiene styrene, polypropylene, and other suitable plastics; or (c) ceramics such as silicon carbide, tungsten carbide, apatite, and other suitable ceramics; wherein the material has the tensile strength to maintain the manufactured structure and can be sterilized for medical use. One of ordinary skill in the art is necessarily familiar with the indicated range of alternative materials that have the identified characteristics associated with their suitability for the identified use. In an embodiment, the dorsal handle piece 80 is made of acrylonitrile-butadiene styrene and includes four interference fit posts 84.

Figure 10:
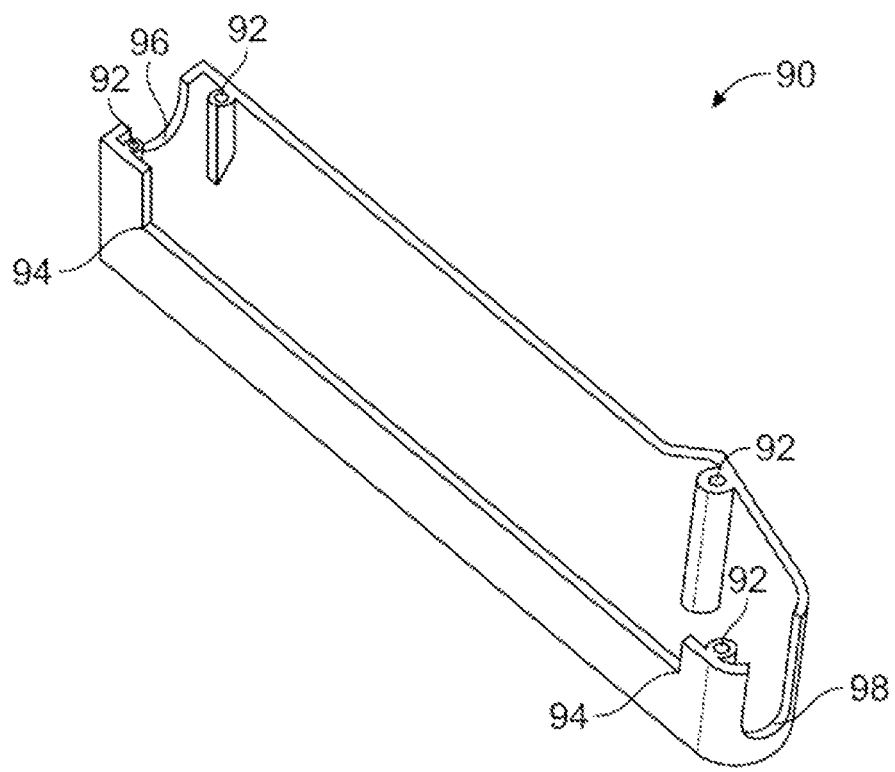
FIG. 10 is a perspective view of the ventral handle piece.

The ventral handle piece 90, as shown in FIG. 10, includes a plurality of sockets 92 that receive the interference frit posts 84 of the dorsal handle piece 80, a track element 94, a proximal ventral recess 96, and a distal ventral recess 98. The ventral handle piece 90 may be made from materials such as any of the following without limitation being intended: (a) metals such as stainless steel, aluminum, and other suitable metals or alloys thereof; (b) polymers such as nylon, polyvinylchloride, polytetrafluoroethylene, polystyrene, acrylonitrile-butadiene styrene, polypropylene, or other suitable plastics; or (c) ceramics such as silicon carbide, tungsten carbide, apatite, or other suitable ceramics; wherein the material has the tensile strength to maintain the manufactured structure and can be sterilized for medical use. One of ordinary skill in the art is necessarily familiar with the indicated range of alternative materials that have the identified characteristics associated with their suitability for the identified use. In one embodiment, the dorsal handle piece 90 is made of acrylonitrile-butadiene styrene and includes four sockets 92.

Figure 11:
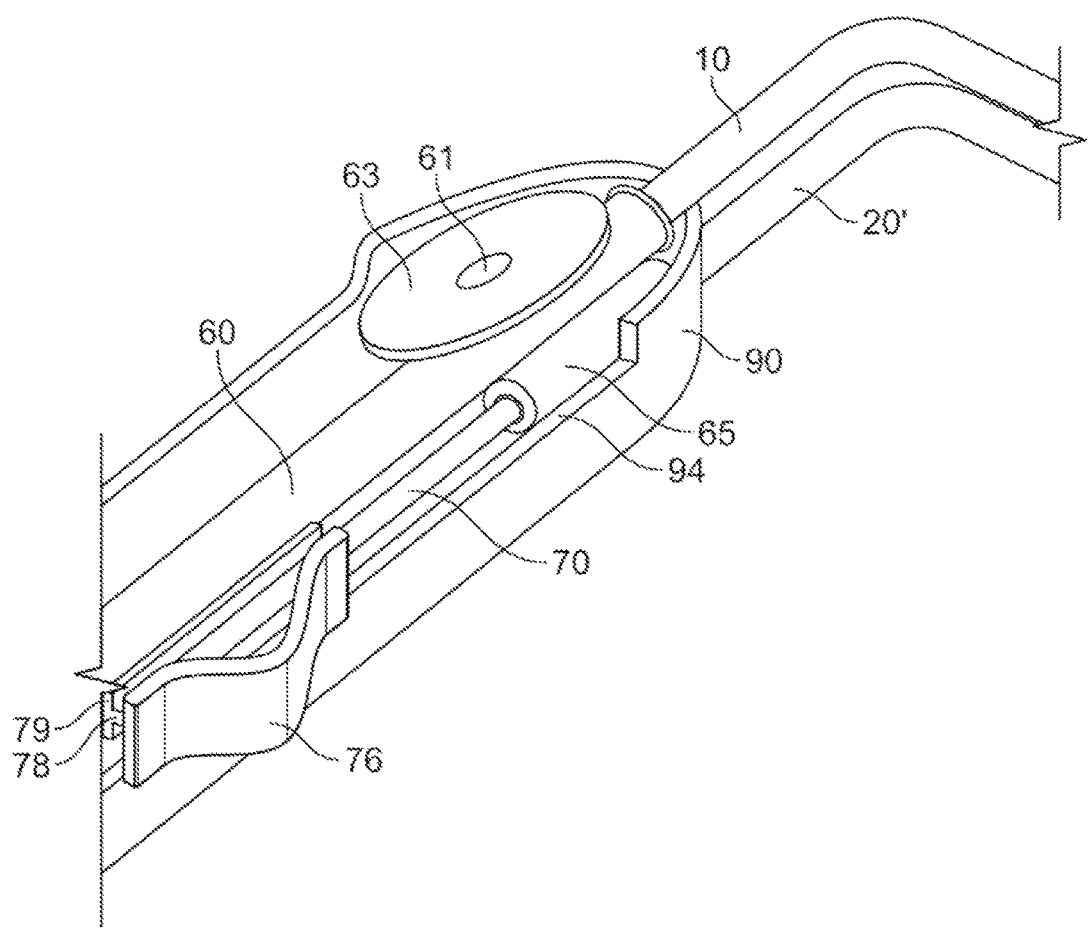
FIG. 11 is a perspective view of the tubular base, stylet, suction tube, and guide tube assembled and disposed in the ventral handle piece.

As shown in FIG. 11, the inner cavity of the ventral handle piece 90 is suitable for disposing the tubular base member 60 and the region proximate to the proximal end 72 of the stylet 70 within its inner cavity. The web 77 of the knob 75 has a proper length known to one of ordinary skill in the art to traverse the width of the track element 94 as shown in FIG. 11, thus allowing accessibility to the node 76 of the knob 75 for urging the connected stylet 70 along the second longitudinal axis 22. The plurality of interference frit posts 84 are inserted to the corresponding sockets 92 of the dorsal handle piece 80 to complete the handle member 100 surrounding the intermediate region 64 and the distal attachment region 66 of the base member 60. After inserting the interference frit posts 84 into the corresponding sockets 92, the dorsal handle piece 80 and ventral handle piece 90 may be welded, glued, and/or frictionally attached to each other. In one embodiment, the dorsal handle piece 80 is glued to the ventral handle piece 90 by a suitable adhesive, e.g., a cyanoacrylate adhesive, such as Loctite 4011 or 4161 Prism manufactured by Henkel. In other embodiments the handle member 100 may be overmolded on the tubular base member 60.

As shown in FIG. 12, the proximal dorsal recess 86 and corresponding proximal ventral recess 96 encircle the tubular base member 60 proximate to the proximal vacuum connector 62 such that the nearness of the proximal dorsal recess 86 and the proximal ventral recess 96 to the outer wall of the tubular base member 60 allows for gluing, welding, and/or frictional attachment.

The distal dorsal recess 88 and distal ventral recess 98 encircle the tubular base member 60 proximate to the distal attachment region 66 such that the nearness of the distal dorsal recess 88 and the distal ventral recess 98 to the outer wall of the tubular base member 60 allows for gluing, welding, and/or frictional attachment.

In one embodiment the dorsal hand piece 80 and the ventral hand piece 90 are glued to the outer wall of the tubular base member 60 at the proximal dorsal recess 86, the proximal ventral recess 96, the distal dorsal recess 88, and distal ventral recess 98 by a suitable adhesive, e.g., a cyanoacrylate adhesive, such as Loctite 4011 or 4161 Prism manufactured by Henkel.

The vent-access opening 82 has dimensions known to one having ordinary skill in the art to surround the vent surrounding member 61 allowing for welding, gluing, and/or frictional attachment. In one embodiment, the vent-access opening 82 is glued to the vent surrounding member 62 by a suitable adhesive, e.g., a cyanoacrylate adhesive, such as Loctite® 4011 or 4161 Prism manufactured by Henkel.

In one embodiment shown in FIG. 1, the proximal vacuum connector 62 of the tubular base member 60 remains exposed.

In one embodiment shown in FIG. 10, the depth of the track element 94 on the ventral handle piece 90 should be suitable so that by disposing the dorsal handle piece 80 on the ventral handle piece 90 limits the knob 75 to displacement that is substantially parallel to the second longitudinal axis 22 along the track element 94. In one embodiment shown in FIG. 11 and FIG. 13, the proper length of the web 77 as known to one having ordinary skill in the art restricts the flange 78 to the interior cavity of the handle member 100 which impedes lateral movement of the knob 75 and further limits the knob 75 to displacement that is substantially parallel to the second longitudinal axis 22 along the track element 94.

Figure 14:
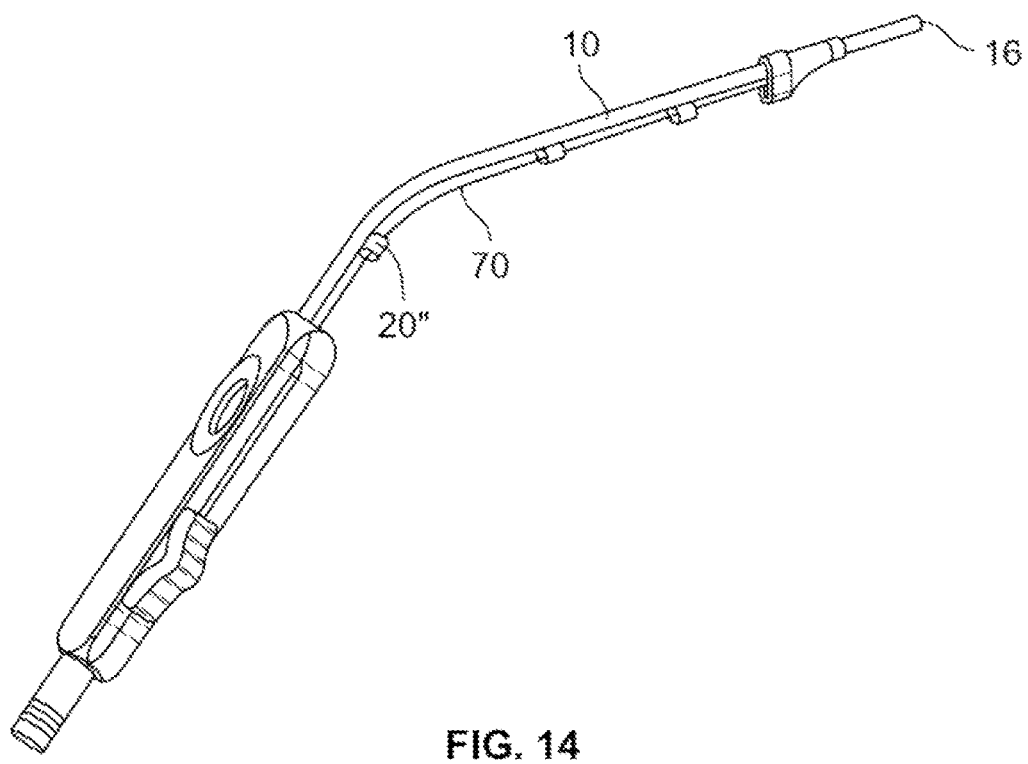
FIG. 14 is a perspective view of an alternative embodiment that utilizes at least one annulus to guide a stylet to a junction conduit.

As shown in FIG. 14, one alternative embodiment of the self-cleaning surgical suction device 1 comprises a guide structure 20 of at least one annulus 20" disposed on the suction tube 10 such that the annulus 20" guides the stylet 70 through the proximal opening 42 of the junction conduit 40 and is substantially coaxial with the second longitudinal axis 22. Furthermore, the annulus 20" should be disposed on the suction tube 10 to provide suitable guidance as the distal end 74 of the stylet 70 is urged in the distal direction substantially along the second longitudinal axis 22. The annulus 20" may be disposed on the suction tube by welding, gluing, or as part of a monolithic mold or cast of the suction tube 10. The annulus 20" may be made from materials such as any of the following without limitation intended: (a) metals such as stainless steel, aluminum, and other suitable metals or alloys thereof; (b) polymers such as nylon, polyvinylchloride, polytetrafluoroethylene, polystyrene, acrylonitrile-butadiene styrene, polypropylene, and other suitable plastics; or (c) ceramics such as silicon carbide, tungsten carbide, apatite, and other suitable ceramics; wherein the suitable metals, alloys, plastics, or ceramics respectively have a tensile strength sufficient to maintain a annular structure and are capable of being sterilized for medical use. One of ordinary skill in the art is necessarily familiar with the indicated range of alternative materials that have the identified characteristics associated with their suitability for the identified use.

Figure 15:
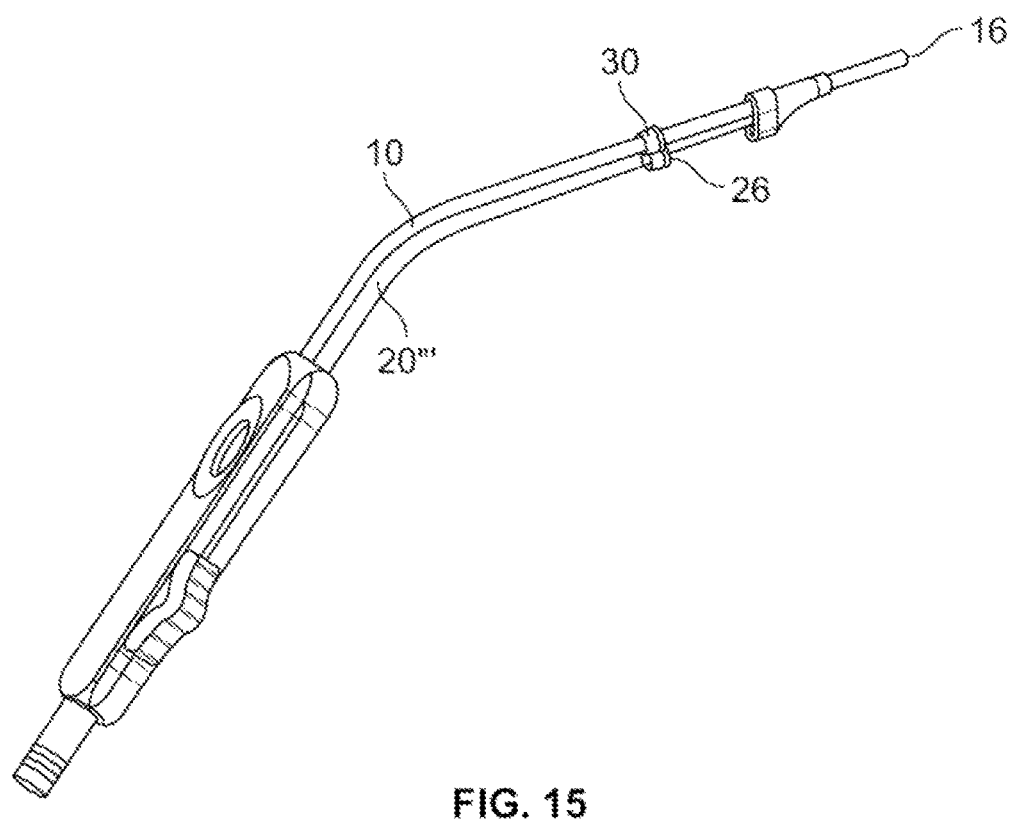
FIG. 15 is a perspective view of an alternative embodiment wherein a shortened guide tube guides a stylet into a junction conduit.

As shown in FIG. 15, one alternative embodiment of the self-cleaning surgical suction device 1 comprises a guide structure 20 in the form of a shortened guide tube 20''' having a second longitudinal axis 22, a proximal opening 24, and distal opening 26. The shortened guide tube 20''' may be made from materials such as any of the following, without limitation intended: (a) metals, such as stainless steel, aluminum, and other suitable metals or alloys thereof; (b) polymers, such as nylon, polyvinylchloride, polytetrafluoroethylene, polystyrene, acrylonitrile-butadiene styrene, polypropylene, and other suitable plastics; or (c) ceramics, such as silicon carbide, tungsten carbide, apatite, and other suitable ceramics; wherein the suitable metals, alloys, plastics, or ceramics respectively have a tensile strength sufficient to maintain a tubular structure and are capable of being sterilized for medical use. One of ordinary skill in the art is necessarily familiar with the indicated range of alternative materials that have the identified characteristics associated with their suitability for the identified use.

The shortened guide tube 20''' may be substantially parallel to the suction tube 10. The suction tube 10 and shortened guide tube 20''' may be conjoined by the bracket 30 proximate to the distal opening 16 of the suction tube 10 and the distal opening 26 of the shortened guide tube 20''', as illustrated by the completed assembly in FIG. 15. The bracket 30 may be disposed at the distal end of the suction tube 10 and shortened guide tube 20''' by overmolding, frictional attachment, welding, and/or glued around the suction tube 10 and shortened guide tube 20'''.

In the depicted embodiment of FIG. 15, the proximal opening 24 is in contact with the receiving member 65 by way of inserting the proximal end of the shortened guide tube 20''' into the receiving member 65 through the distal receiving member opening 69. The shortened guide tube 20''' may be set within the receiving member 65 by welding or adhesives such that the receiving member 65 is coaxial with the shortened guide tube 20''' along the second longitudinal axis 22. In one alternative embodiment, the shortened guide tube 20''' is set within the receiving member 65 by a suitable adhesive, e.g., a cyanoacrylate adhesive, such as Loctite 4011 or 4161 Prism manufactured by Henkel. Alternative embodiments not shown include a connection such that the receiving member 65 is set within the shortened guide tube 20''' by welding or adhesives such that the receiving member 65 is coaxial with the shortened guide tube 20''' along the second longitudinal axis 22.

Figure 16:
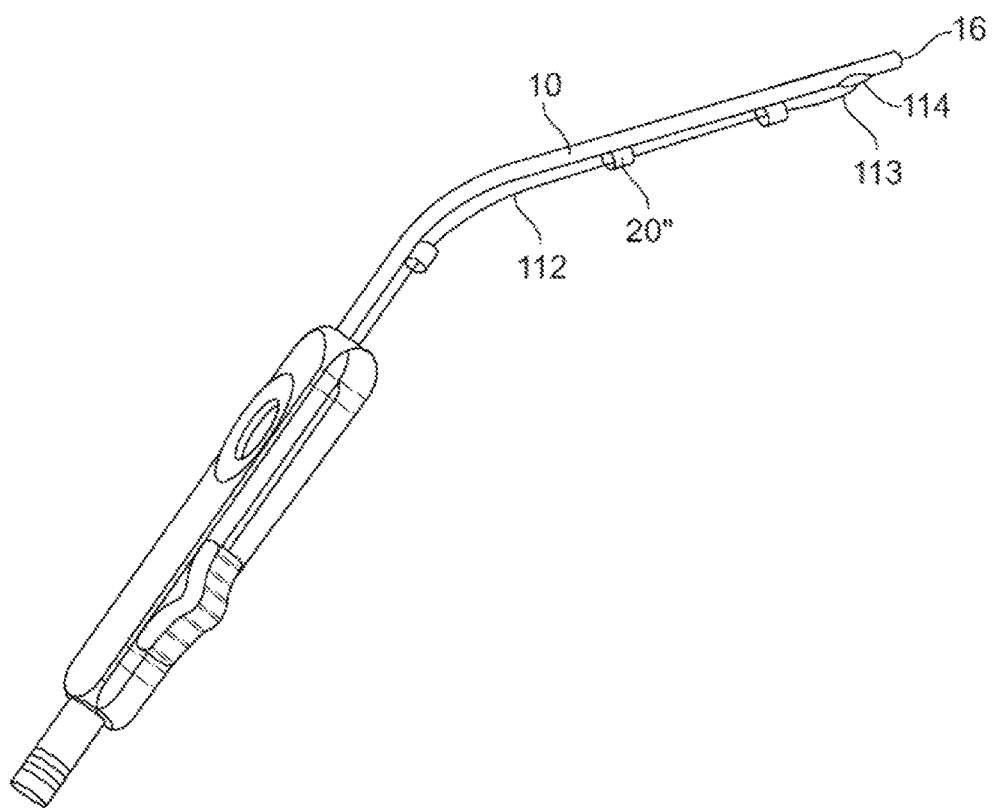
FIG. 16 is a perspective view of an alternative embodiment wherein at least one annulus is used to maintain a hooked end of a stylet in an entry port near a distal opening of a suction tube.

Another alternative embodiment of the self-cleaning surgical suction device 1, as shown in FIG. 16, does not incorporate the junction conduit 40. Instead, a hooked stylet 112 is guided by a guide structure 20 of at least one annulus 20" so that a hooked distal end 113 of the hooked stylet 112 is disposed within the entry port 114 disposed proximate to the distal end of the suction tube 10. The annulus 20" may be disposed on the suction tube by welding, gluing, or as part of a monolithic mold or cast of the suction tube 10. As the hooked stylet 112 is urged in the distal direction substantially along the second longitudinal axis 22 through the annulus 20", the curvature of the hooked distal end 113 meeting resistance from the distal edge of the entry port 114 translates the hooked stylet 112 into the suction tube 10 and to the distal opening 16 of the suction tube 10.

The hooked stylet 112 may be made from materials such as any of the following without limitation intended: (a) metals such as stainless steel, aluminum, and other suitable metals or alloys thereof, or (b) polymers such as polyvinylchloride, polytetrafluoroethylene, polystyrene, acrylonitrile-butadiene styrene, polypropylene, and other suitable plastics; wherein the suitable metals, alloys, or plastics respectively have the suitable elasticity for non-linear movement, suitable shape memory to retain a hooked disposition at the distal end of the hooked stylet 112, and can be sterilized for medical use. One of ordinary skill in the art is necessarily familiar with the indicated range of alternative materials that have the identified characteristics associated with their suitability for the identified use. The annulus 20" can be made from materials as described herein.

Figure 17:
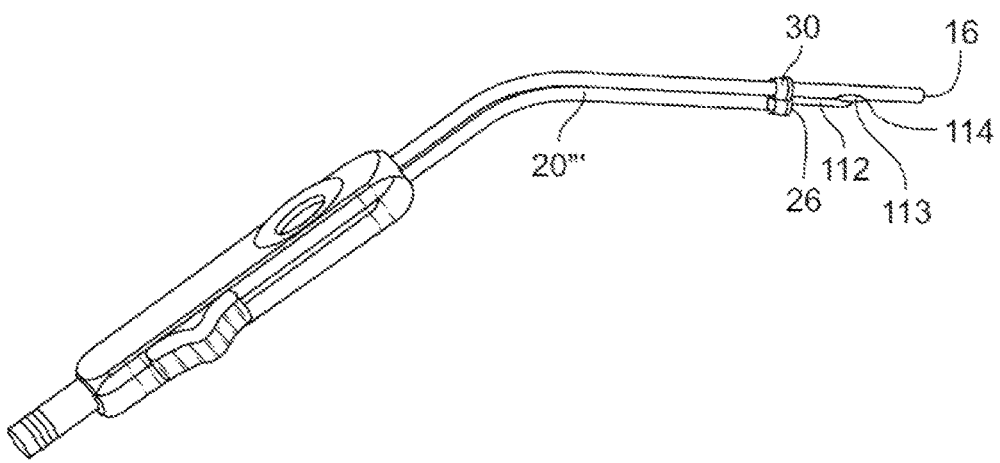
FIG. 17 is a perspective view of an alternative embodiment wherein a shortened guide tube is used to maintain a hooked end of a stylet in an entry port near a distal opening of a suction tube.

Another alternative embodiment of the self-cleaning surgical suction device 1, as shown in FIG. 17, does not incorporate the junction conduit 40. Instead, a hooked stylet 112 is guided by a guide structure 20 in the form of a shortened guide tube 20''' so that a hooked distal end 113 of the hooked stylet 112 is disposed within the entry port 114 disposed proximate to the distal end of the suction tube 10. The suction tube 10 and shortened guide tube 20''' may be conjoined by the bracket 30 proximate to the distal opening 16 of the suction tube 10 and the distal opening 26 of the shortened guide tube 20''', as illustrated by the completed assembly in FIG. 15. The bracket 30 may be disposed at the distal end of the suction tube 10 and shortened guide tube 20''' by overmolding, frictional attachment, welding, and/or glued around the suction tube 10 and shortened guide tube 20'''. As the hooked stylet 112 is urged in the distal direction substantially along the second longitudinal axis 22, the curvature of the hooked distal end 113 meeting resistance from the distal edge of the entry port 114 translates the hooked stylet 112 into the suction tube 10 and to the distal opening 16 of the suction tube 10. The hooked stylet 112 may be made from materials as described herein. The shortened guide tube 20''' can be made from materials as described herein.

Figure 18:
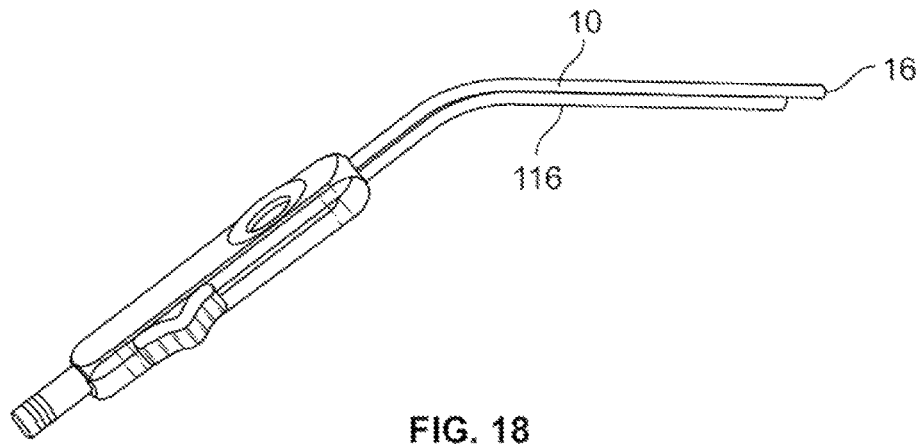
FIG. 18 is a perspective view of an alternative embodiment of the invention wherein an alternative guide tube can feed a stylet directly into a suction tube near a distal opening of a suction tube.

An alternative embodiment of the self-cleaning surgical suction device 1, as shown in FIG. 18, does not incorporate the junction conduit 40 or the tubular tip 50. Instead, the alternative embodiment of FIG. 14 comprises a guide structure 20 in the form of an alternative guide tube 116 having a longitudinal axis (not shown) which intersects the first longitudinal axis 12, a proximal opening (not shown), and a distal opening (not shown) that is in contact with an entry port 114, as shown in FIG. 16, which is disposed proximate to the distal end of the suction tube 10. The alternative guide tube 116 may be substantially parallel to the suction tube 10 until the distal opening contacts the entry port 114. Urging the stylet 70 along the longitudinal axis of the alternative guide tube 116 translates the distal end 74 of the stylet 70 through the entry port 114 of the suction tube 10 and to the distal opening 16 of the suction tube 10.

The alternative guide tube 116 may be made from materials such as any of the following without limitation intended: (a) metals such as stainless steel, aluminum, and other suitable metals or alloys thereof; (b) polymers such as polyvinylchloride, polytetrafluoroethylene, polystyrene, acrylonitrile-butadiene styrene, polypropylene, and other suitable plastics; or (c) ceramics such as silicon carbide, tungsten carbide, apatite, and other suitable ceramics; wherein the suitable metals, alloys, plastics, or ceramics respectively have a tensile strength sufficient to maintain a tubular structure and are capable of being sterilized for medical use. One of ordinary skill in the art is necessarily familiar with the indicated range of alternative materials that have the identified characteristics associated with their suitability for the identified use.

Figure 19:
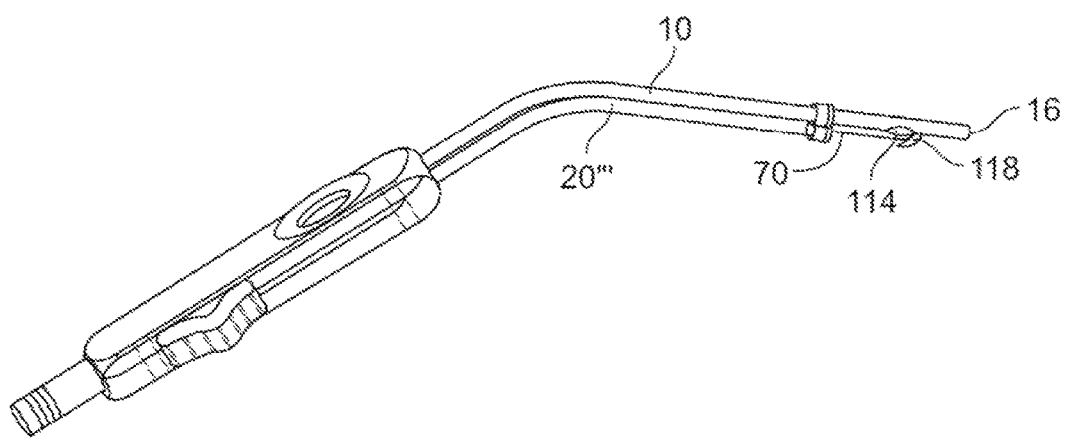
FIG. 19 is a perspective view of an alternative embodiment of the invention wherein a shortened guide tube guides a stylet to a lip.

As shown in FIG. 19, another alternative embodiment of the self-cleaning surgical suction device 1 does not incorporate the junction conduit 40 or the tubular tip 50. Instead, the alternative embodiment depicted in FIG. 19 comprises a lip 118 which functions to translate the distal movement of the stylet 70 into the entry port 114 and to the distal opening 16 of the suction tube 10. As the stylet 70 is urged through the guide structure 20 in the form of a shortened guide tube 20''', a lip 118 disposed about the distal end of the entry port 114 guides the distal end 74 along an interior slope or curvature of the lip 118 into the entry port 114 and to the distal opening 16 of the suction tube 10. The lip 118 may be disposed about the distal end of the entry port 114 as a part of the monolithic suction tube 10 structure, it may be glued about the distal end of the entry port 114, or it may be welded about the distal end of the entry port 114.

The lip 118 may be made from materials such as any of the following without limitation intended: (a) metals such as stainless steel, aluminum, and other suitable metals or alloys thereof; (b) polymers such as polyvinylchloride, polytetrafluoroethylene, polystyrene, acrylonitrile-butadiene styrene, polypropylene, and other suitable plastics; or (c) ceramics such as silicon carbide, tungsten carbide, apatite, and other suitable ceramics; wherein the suitable metals, alloys, plastics, or ceramics respectively have a tensile strength sufficient to provide suitable resistance to the translation movement of the stylet 70 such that the distal end 74 of the stylet 70 may move along the interior slope or curvature of the lip 118 structure and are capable of being sterilized for medical use. One of ordinary skill in the art is necessarily familiar with the indicated range of alternative materials that have the identified characteristics associated with their suitability for the identified use.

The suction tube 10 and shortened guide tube 20''' may be conjoined by the bracket 30 proximate to the distal opening 16 of the suction tube 10 and the distal opening 26 of the shortened guide tube 20''', as illustrated by the completed assembly in FIG. 19. The bracket 30 may be disposed at the distal end of the suction tube 10 and shortened guide tube 20''' by overmolding, frictional attachment, welding, and/or glued around the suction tube 10 and shortened guide tube 20'''.

Figure 20:
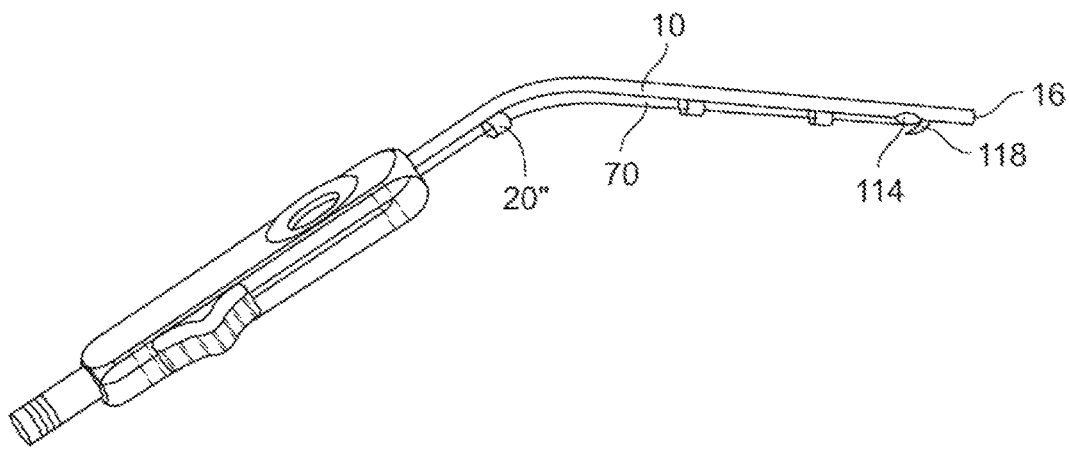
FIG. 20 is a perspective view of an alternative embodiment of the invention wherein at least one annulus guides a stylet to a lip.

Yet another alternative embodiment of the self-cleaning surgical suction device 1, as shown in FIG. 20, also does not incorporate the junction conduit 40 or the tubular tip 50. Similar to a prior embodiment shown in FIG. 19, the alternative embodiment depicted in FIG. 20 comprises a lip 118 which functions to translate the distal movement of the stylet 70 into the entry port 114 and to the distal opening 16 of the suction tube 10. However, the guide structure 20 is at least one annulus 20". The annulus 20" may be disposed on the suction tube by welding, gluing, or as part of a monolithic mold or cast of the suction tube 10.

As the stylet 70 is urged through at least one annulus 20", a lip 118 disposed about the distal end of the entry port 114 guides the distal end 74 along an interior slope or curvature of the lip 118 into the entry port 114 and to the distal opening 16 of the suction tube 10. The lip 118 may be disposed about the distal end of the entry port 114 as a part of the monolithic suction tube 10 structure, it may be glued about the distal end of the entry port 114, or it may be welded about the distal end of the entry port 114. The lip 118 may be made from materials as described herein.

A common feature shared by the various embodiments described herein above is a method comprising the steps of: (a) urging a stylet 70 through a guide structure 20 along a second longitudinal axis 22; (b) translation of the stylet movement from the second longitudinal 22 axis into the suction tube 10 along a first longitudinal axis 12; and (c) retracting the stylet 70 such that the stylet 70 is disposed substantially within the guide structure 20 substantially along the second longitudinal axis 22. This method can be repeated any number of times, as required to clear obstructions from the surgical suction device of the present invention.

Figure 24A:
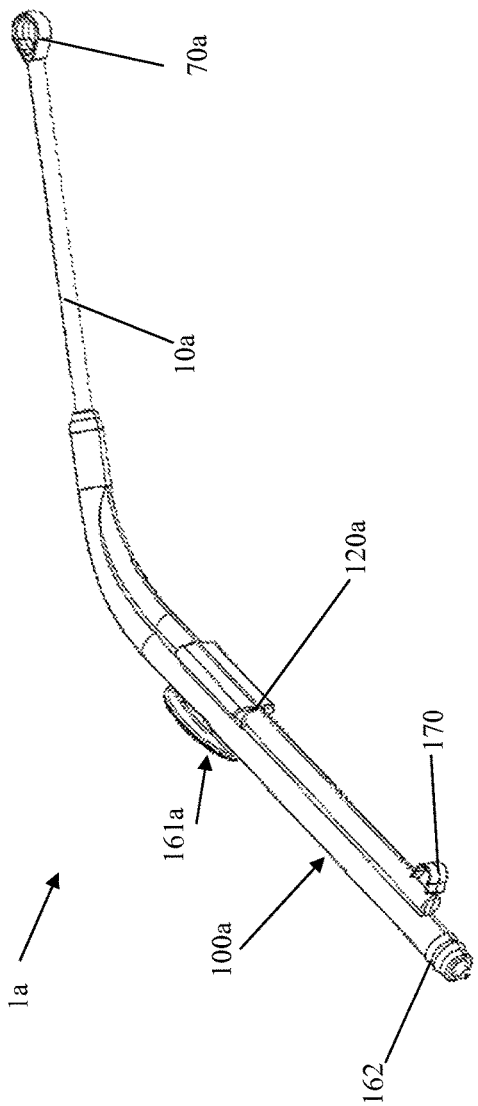
FIG. 24a is a perspective of an alternative embodiment of the invention.
Figure 24B:
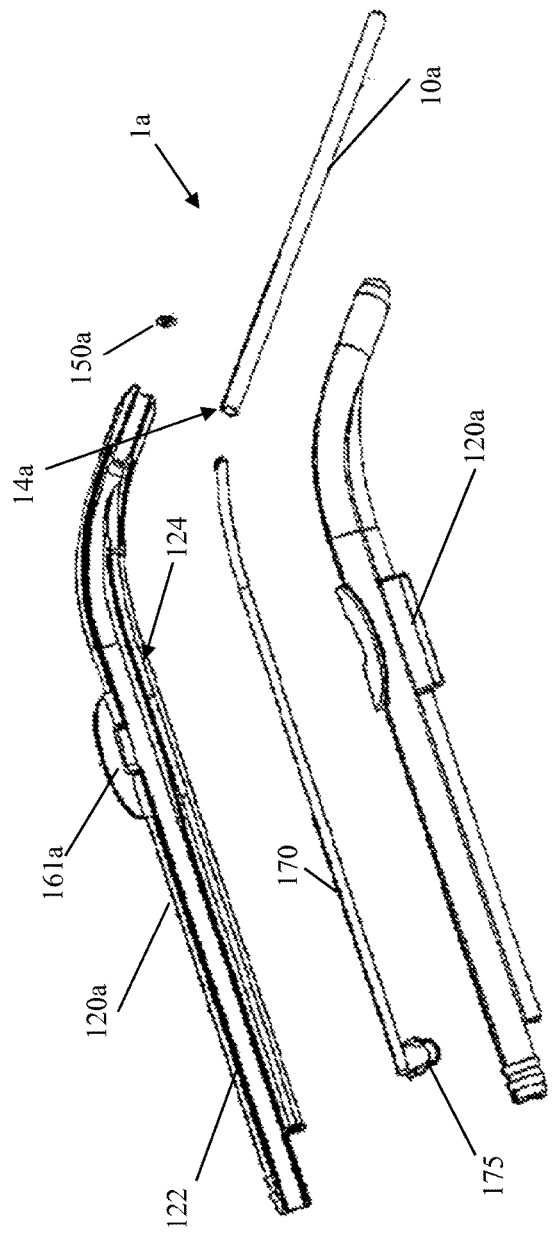
FIG. 24b is an exploded perspective view of an alternative embodiment of the invention where the handle member is split in two separate pieces.
Figure 24E:
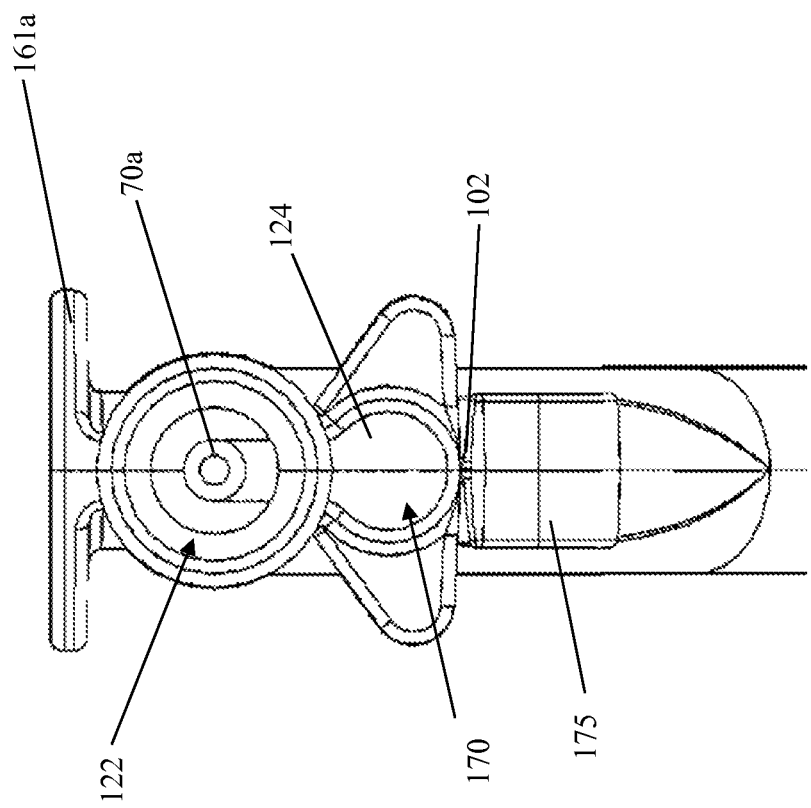
FIG. 24e is a backwards view of an alternative embodiment of the invention.

As shown in FIGS. 24a-24e, another embodiment of a self-cleaning surgical suction device 1a that does not incorporate the junction conduit 40 or the tubular tip 50. The self-cleaning surgical suction device 1a comprises a suction tube 10a, a guide structure 120a, a base member 60a, a stylet 70a, and a handle member 100a; wherein, the guide structure 120a is in the form of a first guide lumen 122 and a second guide lumen 124. In one embodiment, the guide structure is incorporated directly into the structure of the handle member 100a such as to be monolithic mold or cast. Alternatively, the guide structure may be incorporated by way of tubes or tubing disposed within the handle member. The self-cleaning surgical suction device 1a includes a second stylet 170 coaxially disposed within the second guide lumen 124 and longitudinally translatable to the lumen 16a of the suction tube 10a, as shown in FIG. 24c. The second guide lumen 124 functions in a similar fashion as the receiving member 65 and the first guide lumen functions in a similar fashion as the base member 60. The second guide lumen 124 and/or the suction lumen 16a may include a coating material inside the lumen to reduce friction for the first or second stylet 70, 170 longitudinally translating in and out of the second guide lumen 124. Alternatively, the suction lumen 16a may include a coating material as to reduce friction and possible clogging. The coating material may be a silicone coating, Teflon, molybdenum disulfide), graphite or PTFE lubricating solids, carbon coatings, biocompatible coatings, and the like.

The first stylet 70a is coaxially disposed through the first guide lumen 122 and is longitudinally translatable through the first guide lumen 122 and an entry port 14a on the proximal end of the suction lumen 16a. Since the junction conduit 40 is removed, the first guide lumen 122 and the second guide lumen 124 intersect at junction point 40a to allow the second stylet 170 to longitudinally translate into the suction lumen 16a. The junction point 40a functions in a similar fashion as the junction conduit as previously described. The second guide lumen 124 includes an O-ring 150a coaxially disposed around the distal end of the second guide lumen 124 and the second stylet 170 as to prevent backward fluid flow into the second guide lumen 124 from the suction lumen 16a. Alternatively, the O-ring 150a creates an air-tight seal to prevent air leakage between the suction lumen 16a and the second guide lumen 124.

The second stylet 170 is longitudinally translatable within the second guide lumen 124 to coaxially engage the suction lumen 16a and clear the suction lumen 16a from any debris. The second stylet 170 includes a knob 175 similar to the stylet 70 that is longitudinally translatable through a slit or track element 102 disposed within the handle member 100a, as shown in FIG. 24d. A user is able to longitudinally translate the second stylet 170 by pushing the knob 175 to longitudinally move along the slit 102 as to clear the suction lumen 16a. The slit or track element 102 may include several stop points that engage the knob 175 as to prevent longitudinal movement of the second style 170. In an alternative embodiment, the proximal end of the second stylet 170 may be operably coupled to a spring and a clip, whereby the user releases the clip and the spring to longitudinally translate the second stylet 170 through the junction point 40a and distally through the suction lumen 16a. The second stylet 170 may be proximally withdrawn by the user by way of the knob 175 and to re-engage the clip and the spring. A vacuum connector 162 may connect to a vacuum tubing as previously indicated, and the vent 161a may operate as a vent as previously indicated. The stylet 70a may be a rescue-styled stylet with a hoop on the distal end.

Figure 25A:
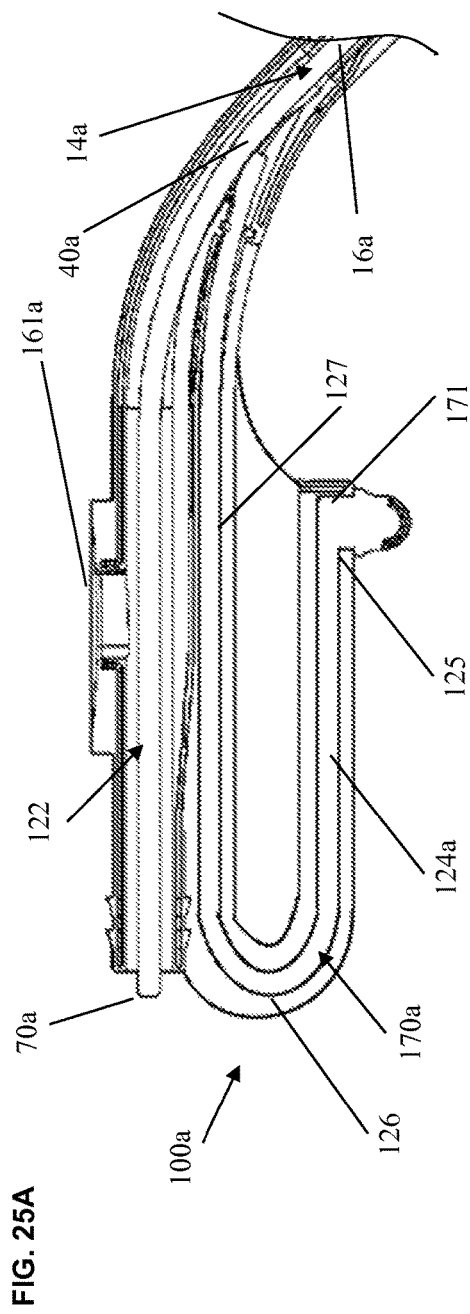
FIG. 25a is a cross-section side view of an alternative embodiment of the invention with an alternative second guide lumen and second stylet.

In an alternative embodiment, the second guide lumen 124 may include alternative shapes, configurations, and locations on the handle member 100a. In some embodiments, the handle member 100a may be required to be of a shorter length relative to the second stylet 170. If the handle member 100a is of a shorter length, then the second guide lumen 124 may assume alternative configurations and the second stylet 170 may assume alternative shapes, configurations, and materials to conform to the shorter length handle member 100a but still maintain a sufficient length as to traverse the entire longitudinal length of the a suction tube 10a and suction lumen 16a. As shown in FIG. 25A, the second guide lumen 124a includes a U-shape about the middle portion 126 including a proximal end 125 the curls towards the distal end of the handle member 100a. A distal end 127 of the second guide lumen 124a is substantially parallel with the handle member 100a and the first guide lumen 122. The distal end 127 of the second guide lumen 124a aligns with the junction point 40a as to allow the second stylet 170a to enter the entry port 14a on the proximal end of the suction lumen 16a. The second stylet 170a is coaxially disposed with the second guide lumen 124a and includes a substantially U-shape as to conform to proximal end 125, the middle portion 126, and the distal end 127 of the second guide lumen 124a. A user longitudinally translates the second stylet 170a to move the distal end of the second stylet 170a into the suction lumen 16a and clear any debris contained therein after suctioning from the vent 161a and first guide lumen 122. The user may then longitudinally translate the second stylet 170a back into the second guide lumen 124a and towards the proximal end 125. The second stylet 170a may comprise a material that allows for deformability and elasticity to move along the U-shape of the middle portion 126. The proximal portion 171 of the second stylet 170a may be operably coupled a spring (not shown), that can be released by a clip or the knob on the proximal portion 171 of the second stylet 170a. The U-shaped configuration may effectively cut the length of the handle member 100a in half, such that the second guide lumen is at least about ½ to about ¼ the length of the handle member 100a but includes a sufficient length of the second stylet 170a to traverse the entire longitudinal length of the suction lumen 16a. The U-shaped configuration for the second guide lumen 124a may be included on any side of the handle member 100a. As shown in FIG. 25E, the second guide lumen 124a and the second stylet 170a is included on the side portion of the handle member 100a, such that the U-shaped configuration is on a horizontal track instead of a vertical track as shown in FIG. 25A.

Figure 25B:
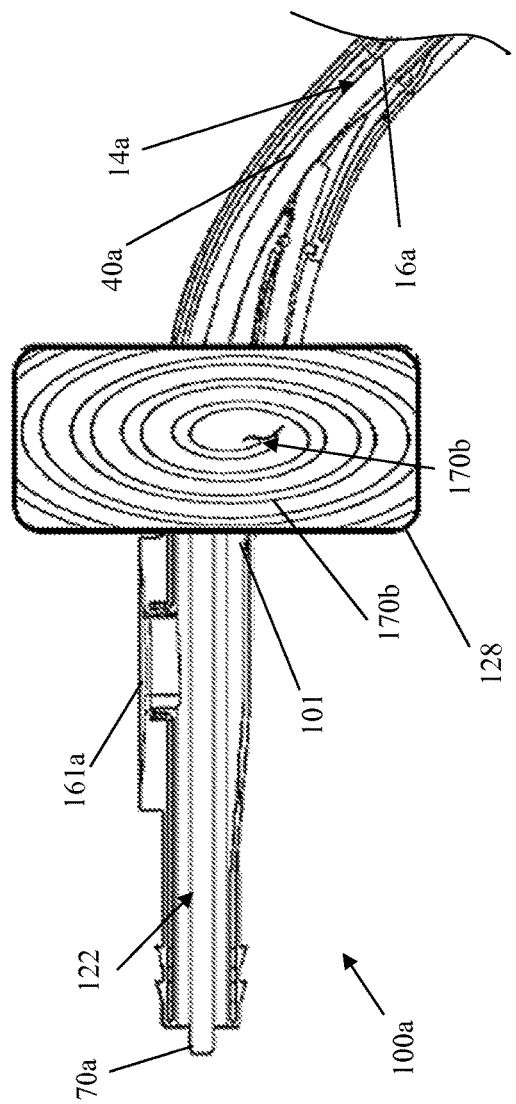
FIG. 25b is a cross-section side view of an alternative embodiment of the invention with an alternative second stylet.

In another embodiment, as shown in FIG. 25B, the second guide lumen may be removed and the second stylet 170b is contained within a ring structure 128 located on the distal end 101 of the handle member 100a. The ring structure 128 is coaxially disposed around the distal end 101 of the handle member 100a and the second stylet 170b is concentrically disposed within the ring structure 128 as to encircle the longitudinal axis of the handle member 100a. Alternatively, the ring structure 128 may be coaxially disposed around any longitudinal portion of the handle member 100a, as preferred by the user or operator. The second stylet 170b includes a ring configuration that expands out of the ring structure 128 by operation of temperature, pressure, superelasticity or shape memory. Nitinol alloys exhibit two closely related and unique properties: shape memory and superelasticity (also called pseudoelasticity). Shape memory is the ability of nitinol to undergo deformation at one temperature, then recover its original, undeformed shape upon heating above its "transformation temperature". Superelasticity occurs at a narrow temperature range just above its transformation temperature; in this case, no heating is necessary to cause the undeformed shape to recover, and the material exhibits enormous elasticity, some 10-30 times that of ordinary metal. When the second stylet 170*b* is to longitudinally traverse the junction point 40*a* and into the suction lumen 16*a*, the second stylet 170*b* transitions from a first state and translates distally through the junction point 40*a* and distally through the suction lumen 16*a* to a second state as to clear the suction lumen 16*a* from any debris after suctioning from the vent 161*a* and the first guide lumen 122. The first state may be determined by a first transition temperature and the second state may be determined by a second transition temperature. The second stylet 170*b* includes a shape memory material having a first radially contracted state and a second radially expanded state. When the region of shape memory material is in the first state, the second stylet is in a ring configuration and is inhibited from translating distally past the junction point 40*a* or into the suction lumen 16*a*, and when the region of shape memory material is in the second state, the second stylet can translate distally past the junction point 40*a* or into the suction lumen 16*a* as to clear any debris from the suction lumen 16*a*. When the second stylet 170*b* transitions from the second state back to the first state, the second stylet 170*b* withdraws from the suction lumen 16*a* and the junction point 40*a* and reverts back to the ring configuration which can only be constrained by the ring structure 128.

The shape memory materials, including shape memory metals and shape memory polymers ("SMM"). The second stylet may be fabricated of shape memory metal alloys, superelastic materials or elastic materials, including, without limitation, titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, cobalt-chromium-molybdenum alloys, nitinol, and stainless steel. Alternatively, biocompatible polymers may be used to fabricate the second stylet. Alternatively, the second stylet 170*b* may be fabricated from elastically deformable materials or plastically deformable materials. Regardless of whether the second stylet 170*b* is made of SMM, elastically or plastically deformable materials, the second stylet 170*b* has a first contracted state such that the second stylet 170*b* is immovable within the second guide lumen 124*b* and the ring structure 128 and a second expanded state such that the second stylet 170*b* is movable relative to the second guide lumen 124*b* and the ring structure 128. The first and second state may be operable through the ring structure 128 such as to change temperature or pressure of the second stylet 170*b* contained there within. Alternatively, the operator may turn the ring structure 128 clockwise as to longitudinally translate the second stylet 170*b* distally towards the junction point 40*a* and through the suction lumen 16. Turning the ring structure 128 counterclockwise longitudinally translates the second stylet 170*b* proximally and retrieves the second stylet 170*b*. The ring structure 128 includes a length at least about ⅕ to about ⅖ the length of the handle member 100*a*, but the second stylet 170*b* contained within the ring structure 128 still maintains a sufficient length to traverse the entire longitudinal length of the suction lumen 16*a*.

Figure 25C:
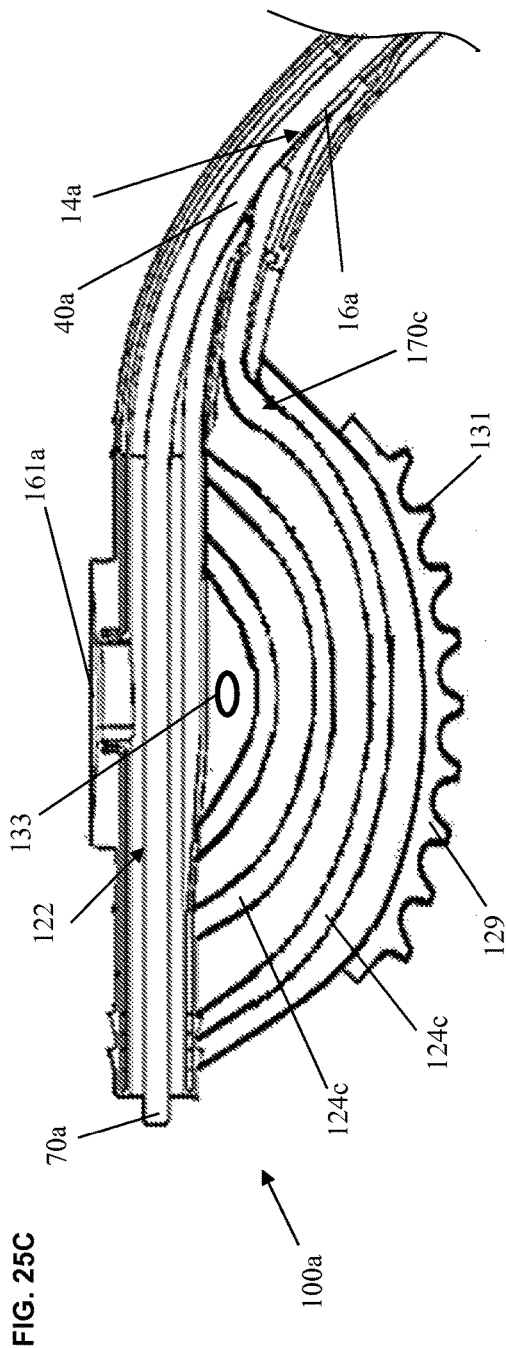
FIG. 25c is a cross-section side view of an alternative embodiment of the invention with an alternative second guide lumen and second stylet.

In another embodiment, as shown in FIG. 25C, the second guide lumen 124*c* is contained with a thumb wheel structure 129 and includes a substantially circular configuration. The thumb wheel structure 129 is mounted to the handle member 100*a* and supports a gear 133 contained therewith. The second stylet 170*c* is coaxially disposed within the second guide lumen 124*c* and is longitudinally translatable by operation of the thumb wheel structure 129. The thumb wheel structure 129 includes a rotatable knob 131 coupled with the second stylet 170*c* and the gear 133, which are adapted to be rotated about a common thumb wheel axis. Rotation of the rotatable knob 131 counterclockwise longitudinally extends the distal end of the second stylet 170*c* into the junction point 40*a* and distally into the suction lumen 16*a*. Rotation of the rotatable knob 131 clockwise retracts the second stylet 170*c* into the second guide lumen 124*c*. The thumb wheel structure 129 decreases the length required for the second guide lumen 124*c* and the handle member 100*a* by at least half, such that the thumb wheel structure 129 is at least about ½ to about ¼ the length of the handle member 100*a*, but includes a sufficient length of the second stylet 170*c* to traverse the entire longitudinal length of the suction lumen 16*a*.

Figure 25D:
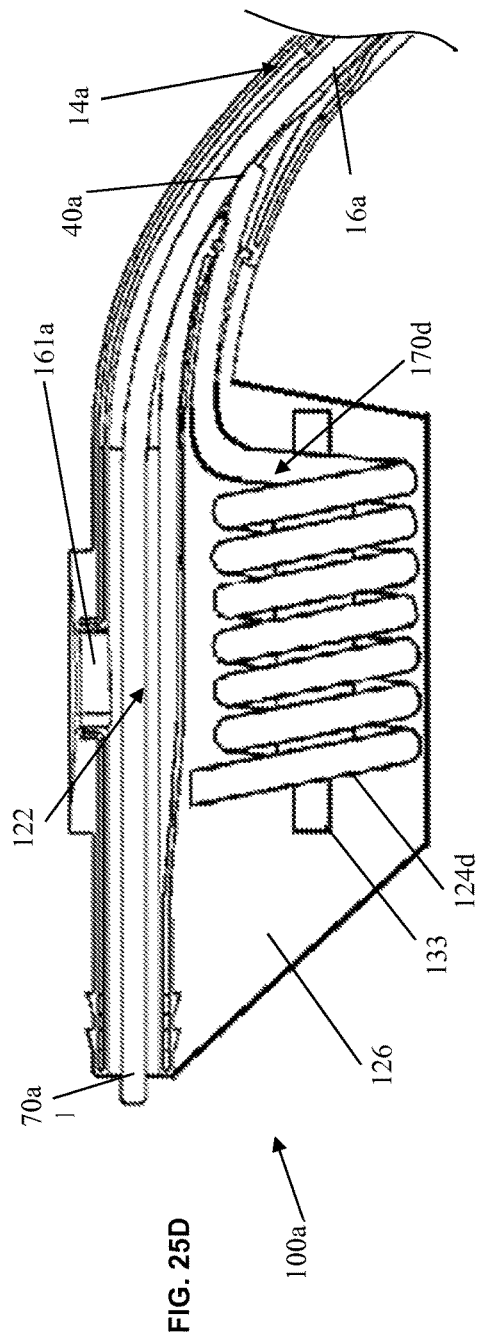
FIG. 25d is a cross-section side view of an alternative embodiment of the invention with an alternative second stylet.

In another embodiment, as shown in FIG. 25D, the second stylet 170*d* includes a substantially helical configuration within the handle member 100*a* and the second guide lumen may be removed from the handle member 100*a*. The second stylet 170*d* includes a nitinol or shape memory configuration as to wrap around a central rod 135 for the helical configuration. The second stylet 170*d* expands out of the second handle member 100*a* by operation of temperature, pressure, superelasticity or shape memory as previously described. When the second stylet 170*d* is to longitudinally traverse the junction point 40*a* and into the suction lumen 16*a*, the second stylet 170*d* transitions from a first state and translates distally through the junction point 40*a* and distally through the suction lumen 16*a* to a second state as to clear the suction lumen 16*a* from any debris after suctioning from the vent 161*a* and the first guide lumen 122. The first state may be determined by a first transition temperature/pressure and the second state may be determined by a second transition temperature/pressure. The second stylet 170*d* includes a shape memory material having a first radially contracted state and a second radially expanded state. When the region of shape memory material is in the first state, the second stylet 170*d* is in a helical configuration wrapped around the central rod 133 and is inhibited from translating distally past the junction point 40*a* or into the suction lumen 16*a*, and when the region of shape memory material is in the second state, the second stylet 170*d* can translate distally past the junction point 40*a* or into the suction lumen 16*a* as to clear any debris from the suction lumen 16*a*. When the second stylet 170*b* transitions from the second state back to the first state, the second stylet 170*d* withdraws from the suction lumen 16*a* and the junction point 40*a* and reverts back to the helical configuration which can only be constrained within the handle member 11*a*. The second stylet 170*d* in the helical configuration decreases the length required for the handle member 100*a* by at least half. The substantially helical configuration in the contracted state includes a length at least about ⅕ to about ⅖ the length of the handle member 100*a*, but the second stylet 170*d* still maintains a sufficient length to traverse the entire longitudinal length of the suction lumen 16*a* in the extended state. The substantially helical configuration for the second guide lumen 124*d* may be included on any side of the handle member 100*a*. As shown in FIG. 25F, the second guide lumen 124*a* and the second stylet 170*d* is included on the side portion of the handle member 100*a*.

The alternative self-cleaning surgical suction device 1*a* may be made from materials such as any of the following without limitation intended: (a) metals such as stainless steel, aluminum, and other suitable metals or alloys thereof;

(b) polymers such as polyvinylchloride, polytetrafluoroethylene, polystyrene, acrylonitrile-butadiene styrene, polypropylene, and other suitable plastics; or (c) ceramics such as silicon carbide, tungsten carbide, apatite, and other suitable ceramics; wherein the suitable metals, alloys, plastics, or ceramics respectively have a tensile strength sufficient to maintain a tubular structure and are capable of being sterilized for medical use. One of ordinary skill in the art is necessarily familiar with the indicated range of alternative materials that have the identified characteristics associated with their suitability for the identified use.

While the present invention has been described in its various embodiments with some degree of particularity, it is understood that this description has been provided only by way of example and that numerous changes in the details of construction, fabrication, and use, including changes in the combination and arrangement of parts or materials, may be made without departing from the spirit and scope of the invention.

What is claimed:

1. A suction device comprising:
   a suction tube having a first longitudinal axis, a proximal opening, a distal opening, and a suction lumen disposed therebetween;
   a guide structure having a first guide lumen and a second guide lumen, wherein the first guide lumen is coaxial with the suction lumen;
   a stylet having a proximal end and a distal end, wherein the stylet is coaxially disposed within the second guide lumen, wherein the second guide lumen includes a proximal end, a middle section, and a distal end, and the middle section includes a U-shape portion and the stylet is longitudinally translatable through the middle section;
   a junction point intersecting the distal opening of the first guide lumen and the distal opening of the second guide lumen, and axial movement of the stylet through the second guide lumen along the second longitudinal axis through the junction point translates the distal end of the stylet into the suction lumen;
   a handle member that surrounds the guide structure which includes a slit element extending parallel to the second longitudinal axis that is proximate to a distal attachment region, and a vent-access opening in fluid communication with the first guide lumen such that a vent and a vent-surrounding member are accessible through the vent-access opening, wherein the second guide lumen is ½ to ¼ the length of the handle and the stylet includes a length to traverse the entire longitudinal length of the suction tube;
   wherein the handle member further comprising a vacuum connector on the distal end and, an intermediate region, the distal attachment region, and the vent disposed on the intermediate region in fluid communication with the vacuum connector, wherein the distal attachment region is in contact with the proximal opening of the suction tube such that the proximal vacuum connector is in fluid communication with the suction tube, and wherein the handle member further comprises the vent-surrounding member disposed on the intermediate region; and
   wherein the stylet is a rescue-style stylet with a hoop on the distal end and coaxially disposed within the first guide lumen and longitudinally translatable there within.

2. The device of claim 1, further comprising an O-ring coaxially disposed within the distal end of the second guide lumen as to prevent a vacuum leak.

3. The device of claim 2, wherein the stylet includes a knob to longitudinally translate the stylet through the second guide lumen.

\* \* \* \* \*